United States Patent
Le Fur et al.

(10) Patent No.: US 10,981,912 B2
(45) Date of Patent: Apr. 20, 2021

(54) MACROCYCLIC LIGANDS WITH PICOLINATE GROUP(S), COMPLEXES THEREOF AND ALSO MEDICAL USES THEREOF

(71) Applicants: GUERBET, Villepinte (FR); UNIVERSITE DE BRETAGNE OCCIDENTALE, Brest (FR); CENTRE NATIONAL DE LA RECHERCHE SCIENTIFIQUE, Paris (FR)

(72) Inventors: Mariane Le Fur, Brest (FR); Raphaël Tripier, Kersaint Plabennec (FR); Olivier Rousseaux, Senlis (FR); Maryline Beyler, Brest (FR)

(73) Assignees: GUERBET, Villepinte (FR); UNIVERSITE DE BRETAGNE OCCIDENTALE, Brest (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/658,377

(22) Filed: Oct. 21, 2019

(65) Prior Publication Data
US 2020/0123155 A1    Apr. 23, 2020

Related U.S. Application Data

(62) Division of application No. 16/065,661, filed as application No. PCT/EP2016/082644 on Dec. 23, 2016, now Pat. No. 10,711,001.

(30) Foreign Application Priority Data

Dec. 24, 2015 (FR) ..................... 1563346

(51) Int. Cl.
| | | |
|---|---|---|
| *C07D 471/08* | (2006.01) | |
| *C07D 471/18* | (2006.01) | |
| *A61K 31/439* | (2006.01) | |
| *A61K 36/66* | (2006.01) | |
| *A61K 45/06* | (2006.01) | |

(52) U.S. Cl.
CPC .......... *C07D 471/18* (2013.01); *A61K 31/439* (2013.01); *A61K 36/66* (2013.01); *A61K 45/06* (2013.01); *C07D 471/08* (2013.01)

(58) Field of Classification Search
CPC ... C07D 471/08; C07D 471/18; A61K 31/439
See application file for complete search history.

(56) References Cited

FOREIGN PATENT DOCUMENTS

EP    0391766 A1    10/1990

OTHER PUBLICATIONS

Jean-Michel Siague et al., Regioselective synthesis of N-functionalized 12-membered azapyridinomacrocycles bearing trialkylcarboxylic acid side chains, Tetrahedron, 57, 4713-4718. (Year: 2001).*
Jean-Michel Siaugue et al., Regioselective synthesis of N-functionalized 12-membered azapyridinomacrocycles bearing trialkylcarboxlic acid side chains, Tetrahderon, 57, 4713-4718. (Year: 2001).*
Aime et al., "Designing Novel Contrast Agents for Magnetic Resonance Imaging. Synthesis and Relaxometric Characterization of three Gadolinium (III) Complexes Based on Functionalized Pyridine-Containing Macrocyclic Ligands", Helvetica Chimica Acta, 2003, pp. 615-632, vol. 86.
Bellouard et al., "cis-Diprotected Cyclams and Cyclens: A New Route to Symmetrically or Asymmetrically 1,4-Disubstituted Tetraazamacrocycles and to Asymmetrically Tetrasubstituted Derivatives," J. Chem. Soc., Perkin Trans. 1, 1999, pp. 3499-3505.
Borbas et al., "Synthesis of Asymmetrically Substituted Cyclen-Based Ligands for the Controlled Sensitisation of Lanthanides", Org. Biol. Chem, 2007, pp. 2274-2282, vol. 5.
Richman et al., "Nitrogen Analogs of Crown Ethers", Journal of the American Chemical Society, Apr. 3, 1974, pp. 2268-2270, vol. 96, Issue 7.

(Continued)

*Primary Examiner* — Michael G. Hartley
*Assistant Examiner* — Jagadishwar R Samala
(74) *Attorney, Agent, or Firm* — Steven M. Ritchey; Thompson Coburn LLP

(57) ABSTRACT

A macrocycle compound of general formula (X)

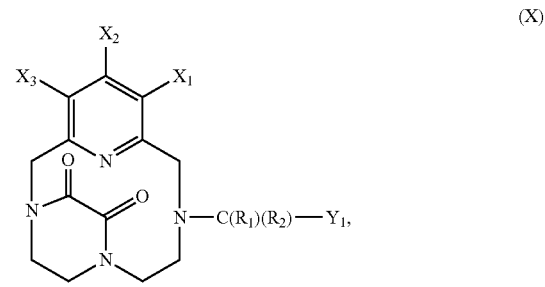

in which $Y_1$ represents a C(O)OH group or a group of formula (II)

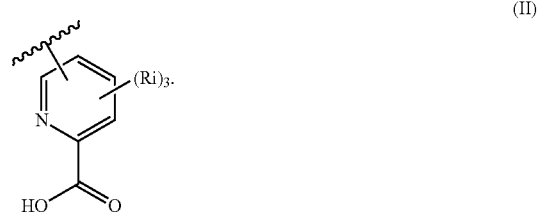

15 Claims, 4 Drawing Sheets

(56) References Cited

OTHER PUBLICATIONS

Stetter et al., "Darstellung Und Komplexbildung Von Polyazacycoalkan-N-Essigsauren", Tetraherdon, 1981, pp. 767-772, vol. 37, Issue 4.
Tircso et al., "Equilibrium and Formation/Dissociation Kinetics of Some LnIIIPCTA Complexes", Inorganic Chemistry, 2006, pp. 9269-9280, Issue 45.
Uozumi, Y., "C—C Bond-Forming Reactions via Cross-Coupling", Comprehensive Chirality, 2012, pp. 18-31, vol. 4.

* cited by examiner

MACROCYCLIC LIGANDS WITH PICOLINATE GROUP(S), COMPLEXES THEREOF AND ALSO MEDICAL USES THEREOF

CROSS-REFERENCE TO RELATED APPLICATIONS

This application is a divisional application of U.S. Ser. No. 16/065,661, filed on Jun. 22, 2018, which is a U.S. National Phase application of PCT/EP2016/082644, filed on Dec. 23, 2016, claiming the benefit of French Application No. 1563346, filed on Dec. 24, 2015, each of which is incorporated herein by reference in its entirety.

The present invention relates to novel macrocyclic ligands and also complexes thereof, especially radioactive complexes, and the uses thereof in medical imaging and/or in therapy, especially in interventional radiology.

The present invention also relates to a novel process for preparing ligands such as according to the invention, and also the preparation intermediates thereof.

The need for targeted and personalized treatments in oncology has led to the development of novel therapeutic strategies based on early detection tools combined with more specific and more efficient vectorized treatments.

Interventional radiology is a very promising direction in individualized medicine. It allows combination in the same sequence of precise diagnosis of the lesion or tumor and/or instantaneous treatment thereof, guided and controlled by images. It is described as minimally invasive surgery and can as a result be performed as outpatient treatment, which allows saving of many expensive days of hospitalization for an efficacy that is often comparable with that of conventional surgery. Interventional radiology may thus represent an alternative or a complement to conventional surgical treatment.

Interventional radiology allows access to a lesion or tumor located inside the body to perform a diagnostic action (for example sampling) or a therapeutic action. Imaging by fluoroscopy, echography, scanner or MRI allows pinpointing, guiding and optimum control of the medical gesture.

There is thus a need for novel molecules that can be used in medical imaging and/or in therapy, in particular in interventional radiology. More particularly, there is a need for ligands which can complex chemical elements, in particular metals, so as to obtain complexes that can be used in medical imaging and/or in therapy, in particular in interventional radiology.

Such ligands must especially be stable and must complex metals strongly enough for them to reach their target without diffusing into other sensitive organs or tissues such as bone, the lungs and the kidneys.

The aim of the present invention is to provide novel ligands for complexing chemical elements, in particular radioelements.

The aim of the present invention is also to provide novel complexes, in particular radioactive complexes.

The aim of the present invention is to provide ligands and/or complexes that are particularly useful in medical imaging and/or in therapy, especially in cancer treatment.

The aim of the present invention is also to provide a pharmaceutical composition comprising complexes which allow the medical imaging, targeting and/or treatment of cancers.

The aim of the present invention is to provide a novel process for preparing these ligands.

The present invention relates to a compound of general formula (I) below:

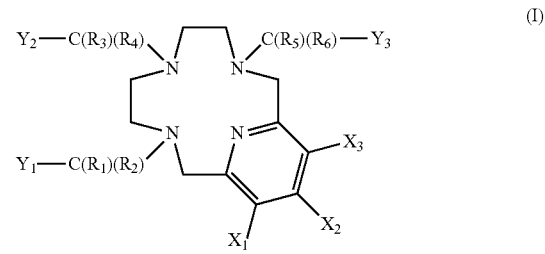

in which:
R$_1$, R$_2$, R$_3$, R$_4$, R$_5$ and R$_6$ represent, independently of each other, H, a (C$_1$-C$_{20}$)alkyl group or a (C$_1$-C$_{20}$)alkylene-(C$_6$-C$_{10}$)aryl group;
said alkyl, alkylene and aryl groups possibly being substituted with one or more substituents chosen from organic acid functions, preferably from the group constituted by —COOH, —SO$_2$OH, —P(O)(OH)$_2$ and —O—P(O)(OH)$_2$;
X$_1$, X$_2$ and X$_3$ are chosen, independently of each other, from the group constituted by: H, —C(O)N(Re)(Rd), (C$_1$-C$_{20}$)alkyl, (C$_2$-C$_{20}$)alkenyl, (C$_2$-C$_{20}$)alkynyl and (C$_6$-C$_{10}$)aryl, with Re and Rd being, independently of each other, H or a (C$_1$-C$_{20}$)alkyl group,
said alkyl, alkenyl and alkynyl groups possibly comprising one or more heteroatoms and/or one or more (C$_6$-C$_{10}$) arylenes in their chain and possibly being substituted with a (C$_6$-C$_{10}$)aryl;
said alkyl, alkenyl, alkynyl and aryl groups possibly being substituted with one or more substituents chosen from organic acid functions, preferably from the group constituted by —COOH, —SO$_2$OH, —P(O)(OH)$_2$ and —O—P(O)(OH)$_2$;
Y$_1$, Y$_2$ and Y$_3$ represent, independently of each other, a C(O)OH group or a group of formula (II) below:

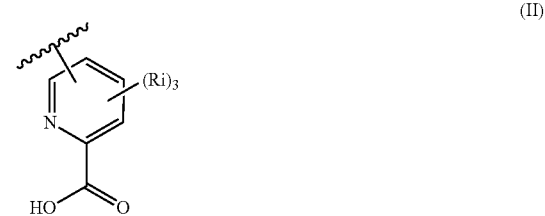

in which:
the radicals Ri are chosen, independently of each other, from the group constituted by:
H, halogen, N$_3$, (C$_1$-C$_{20}$)alkyl, (C$_2$-C$_{20}$)alkenyl, (C$_2$-C$_{20}$) alkynyl and (C$_6$-C$_{10}$)aryl, said alkyl, alkenyl and alkynyl groups possibly comprising one or more heteroatoms and/or one or more (C$_6$-C$_{10}$)arylenes in their chain and possibly being substituted with a (C$_6$-C$_{10}$)aryl;
said alkyl, alkenyl, alkynyl and aryl groups possibly being substituted with one or more substituents chosen from organic acid functions, preferably from the group constituted by —COOH, —SO$_2$OH, —P(O)(OH)$_2$ and —O—P(O)(OH)$_2$;
and
at least one of the radicals Y$_1$, Y$_2$ and Y$_3$ being a group of formula (II);
or a pharmaceutically acceptable salt thereof.

According to one embodiment, the present invention relates to a compound of general formula (I) below:

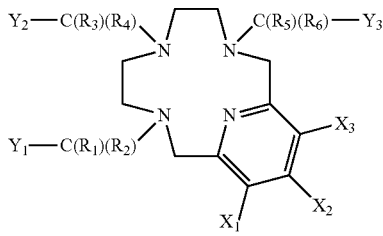

in which:
- $R_1$, $R_2$, $R_3$, $R_4$, $R_5$ and Re represent, independently of each other, H, a ($C_1$-$C_{20}$)alkyl group or a ($C_1$-$C_{20}$)alkylene-($C_6$-$C_{10}$)aryl group;
- $X_1$, $X_2$ and $X_3$ are chosen, independently of each other, from the group constituted by: H, —C(O)N(Re)(Rd), ($C_1$-$C_{20}$)alkyl, ($C_2$-$C_{20}$)alkenyl, ($C_2$-$C_{20}$)alkynyl and ($C_6$-$C_{10}$)aryl, with Re and Rd being, independently of each other, H or a ($C_1$-$C_{20}$)alkyl group,
- said alkyl, alkenyl and alkynyl groups possibly comprising one or more heteroatoms and/or one or more ($C_6$-$C_{10}$)arylenes in their chain and possibly being substituted with a ($C_6$-$C_{10}$)aryl;
- $Y_1$, $Y_2$ and $Y_3$ represent, independently of each other, a C(O)OH group or a group of formula (II) below:

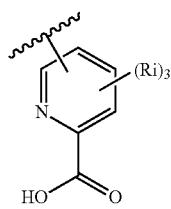

in which:
- the radicals Ri are chosen, independently of each other, from the group constituted by: H, halogen, $N_3$, ($C_1$-$C_{20}$)alkyl, ($C_2$-$C_{20}$)alkenyl, ($C_2$-$C_{20}$)alkynyl and ($C_6$-$C_{10}$)aryl,
- said alkyl, alkenyl and alkynyl groups possibly comprising one or more heteroatoms and/or one or more ($C_6$-$C_{10}$)arylenes in their chain and possibly being substituted with a ($C_6$-$C_{10}$)aryl; and at least one of the radicals $Y_1$, $Y_2$ and $Y_3$ being a group of formula (II);

or a pharmaceutically acceptable salt thereof.

The inventors have developed novel ligand-metal complexes (complexes also known as chelates) from the pyclene macrocycle (3,6,9,15-tetraazabicyclo[9.3.1]pentadeca-1(15),11,13-triene), variously substituted with acetate and/or picolinate groups (6-methylene-2-pyridinecarboxylic acid). The pyclene macrocycle has the following formula:

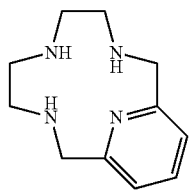 [SMILES: c1cc2nc(c1)CNCCNCCNC2]

Surprisingly, the complexes according to the invention have good thermodynamic stability and also good kinetic inertia. Furthermore, equally surprisingly, the inventors have discovered that the complexes according to the invention can be dissolved in an iodinated oil such as Lipiodol®, which is an iodinated oil manufactured and sold by the company Guerbet and which is constituted by ethyl esters of iodinated fatty acids of poppy oil. Thus, the complexes according to the invention dissolved in an iodinated oil such as Lipiodol® can be vectorized especially toward the liver and can allow the visualization and/or treatment of cancers, for example liver cancer.

These complexes also have a good radiochemical yield for extraction into an iodinated oil such as Lipiodol®. They in particular show good incorporation of radioactivity into an iodinated oil such as Lipiodol® and good stability of the radioactive Lipiodol® solution in in vitro tests.

In particular, the combination of the properties of Lipiodol® vectorization, of therapeutic efficacy of the radioelements and the good tolerability of these products make it possible to propose a therapeutic cancer treatment that is safe and easier to perform.

Vectorization of the complexes according to the invention with an iodinated oil such as Lipiodol® makes it possible especially to avoid poor delivery of the complexes while reducing the risk of adverse effects in healthy organs, in particular healthy liver or in the extra-hepatic organs, and makes it possible to achieve the effective radioactivity dose in the tumor.

More particularly, this vectorization facilitates the work of the interventional radiologist at the time of injection of the complexes according to the invention. For example, during intra-arterial injection monitored by fluoroscopy, the radiologist's gesture will be more precise and safer, allowing adjustment of the rate of delivery of the complexes as a function of the uptake by the tumor of the complexes according to the invention.

DEFINITIONS

The term "ligand" means a compound that is capable of complexing a chemical element such as a metal, preferably a radioelement. According to one embodiment, the ligands within the meaning of the invention are in anionic form and can complex radioelements in cationic form, for example metal cations in oxidation state (III). According to the present invention, the compounds of formula (I) are ligands.

The term "radioelement" means any known radioisotope of a chemical element, whether it is natural or artificially produced. According to one embodiment, the radioelement is chosen from yttrium and lanthanide radioisotopes. The term "lanthanides" denotes atoms chosen from the group constituted by: La, Ce, Pr, Nd, Pm, Sm, Eu, Gd, Tb, Dy, Ho, Er, Tm, Yb and Lu.

The term "complex" means the combination of a ligand as defined above with a chemical element, preferably a radioelement as defined above. The term "complex" is synonymous with "chelate".

The "thermodynamic stability" represents the affinity of the ligand for a given element, in particular a given metal. It is the equilibrium constant for the complexation reaction:
Metal+Ligand ⇌ Complex
the mathematical expression of which is as follows:

$$K = \frac{[\text{Metal}] \times [\text{Ligand}]}{[\text{Complex}]}$$

The values are generally expressed in decimal logarithm form log K. According to one embodiment, the complexes according to the invention have strong affinity. According to one embodiment, the complexes according to the invention have an equilibrium thermodynamic constant at least equal to 16 (log K at least equal to 16).

The complexes formed according to the equilibrium reaction described above are capable of dissociating under the action of various factors (pH, presence of metals or competing ligands). This dissociation may have substantial consequences in the context of using the complexes in human medicine, since it entails release of the metal into the body. In order to limit this risk, slow dissociation complexes are desired, i.e. complexes with good kinetic inertia. The kinetic inertia may be determined via dissociation tests in acidic medium. These experiments lead to the determination for each complex of a half-life time ($T_{1/2}$) under defined conditions.

In the context of the invention, the term "treating", "treatment" or "therapeutic treatment" means reversing, relieving or inhibiting the progress of the disorder or complaint to which this term is applicable, or one or more symptoms of such a disorder.

The term "medical imaging" denotes means for the acquisition and restitution of images of the human or animal body by means of various physical phenomena such as x-ray absorption, nuclear magnetic resonance, ultrasound wave reflection or radioactivity. According to one embodiment, the term "medical imaging" refers to x-ray imaging, MRI (magnetic resonance imaging), single-photon emission tomography (SPECT: single-photon emission computed tomography), positron emission tomoscintigraphy (PET) and luminescence. Preferably, the medical imaging method is x-ray imaging. According to a particular embodiment, the medical imaging method is MRI if the complex according to the invention comprises Gd(III), SPECT if the complex according to the invention comprises a gamma emitter and PET if the complex according to the invention comprises a beta+ emitter.

The capacity of contrast agents to accelerate the rates of relaxation 1/T1 and 1/T2 of the protons of water is measured by means of a magnitude known as relaxivity. The relaxivity (r) of a contrast agent is especially defined as the rate of relaxation, normalized by the concentration of the contrast agent.

The term "($C_1$-$C_{20}$)alkyl" denotes saturated aliphatic hydrocarbons, which may be linear or branched and comprise from 1 to 20 carbon atoms. Preferably, the alkyls comprise from 1 to 15 carbon atoms, for example 6, 7, 8, 9, 10, 11, 12, 13, 14 or 15 carbon atoms. The term "branched" means that an alkyl group is substituted on the main alkyl chain.

The term "($C_1$-$C_{20}$)alkylene" denotes an alkyl radical as defined above, which is divalent.

The term "($C_2$-$C_{20}$)alkene" denotes an alkyl as defined above, comprising at least one carbon-carbon double bond.

The term "($C_2$-$C_{20}$)alkyne" denotes an alkyl as defined above, comprising at least one carbon-carbon triple bond.

The term "($C_6$-$C_{10}$)aryl" denotes monocyclic, bicyclic or tricyclic hydrocarbon-based aromatic compounds, in particular phenyl and naphthyl.

The term "arylene" denotes an aryl as defined above, which is divalent, in particular phenylene and naphthylene.

According to one embodiment, the term "halogen" denotes F, Cl, Br, I and At.

Among the heteroatoms, mention may be made especially of P, N, O and S, preferably N and O. According to a particular embodiment, the compounds of general formula (I) comprise 1 or 2 heteroatoms. Preferably, —O—($C_1$-$C_{20}$)alkyl (also known as alkoxy groups), —O—($C_{2-20}$)alkenyl and —O—($C_{2-20}$)alkynyl groups are present.

The term "Lipiodol" refers to an iodinated oil and preferentially to the pharmaceutical specialty Lipiodol®, which is an injectable solution manufactured and sold by Guerbet and constituted by ethyl esters of iodinated fatty acids of poppy oil. Lipiodol® is a product that is used especially for visualization, localization and/or vectorization in the course of transarterial chemoembolization of hepatocellular carcinoma at the intermediate stage in adults, and also for diagnosis via the selective hepatic arterial route of the hepatic extension of malignant or non-malignant hepatic lesions.

The term "organic acid" (or organic acid function) means an organic compound (or an organic function) which has acidic properties, i.e. which is capable of releasing an $H^+$ or $H_3O^+$ cation in aqueous media. Among the organic acids, mention may be made of carboxylic acids, sulfonic acids, phosphates and phosphonates. The organic acid functions according to the invention are preferably chosen from the group constituted by —COOH, —SO$_2$OH, —P(O)OH, —P(O)(OH)$_2$ and —O—P(O)(OH)$_2$, and more preferentially —COOH. Such acid functions are salifiable and may be in the basic form thereof. In particular, these acid functions are in the form of pharmaceutically acceptable salts, as defined below; for example, in the form of the sodium or meglumine (1-deoxy-1-(methylamino)-D-glucitol or N-methyl-D-glucamine) salt.

The Iodinated Oils

The term "fatty acid" denotes saturated or unsaturated aliphatic carboxylic acids bearing a carbon chain of at least 4 carbon atoms. Natural fatty acids bear a carbon chain of 4 to 28 carbon atoms (generally an even number). The term "long-chain fatty acid" refers to a length of 14 to 22 carbons, and "very-long-chain fatty acid" refers to more than 22 carbons. Conversely, the term "short-chain fatty acid" refers to a length of 4 to 10 carbons, especially 6 to 10 carbon atoms, in particular 8 or 10 carbon atoms. A person skilled in the art knows the associated nomenclature and in particular uses:

Ci-Cp to denote a fatty acid range from Ci to Cp
Ci+Cp, the total of the Ci fatty acids and of the Cp fatty acids For example:
fatty acids of 14 to 18 carbon atoms is written as "$C_{14}$-$C_{18}$ fatty acids"
the total of the C16 fatty acids and of the C18 fatty acids is written as C16+C18
for a saturated fatty acid, a person skilled in the art will use the following nomenclature Ci: 0, in which i is the number of carbon atoms in the fatty acid. Palmitic acid, for example, will be denoted by the nomenclature (C16:0).

for an unsaturated fatty acid, a person skilled in the art will use the following nomenclature Ci; x n-N in which N will be the position of the double bond in the unsaturated fatty acid starting from the carbon opposite the acid group, i is the number of carbon atoms in the fatty acid and x is the number of double bonds (unsaturations) in this fatty acid. Oleic acid, for example, will be denoted by the nomenclature (C18;1 n-9).

Advantageously, the iodinated oil according to the invention comprises or is constituted by iodinated fatty acid derivatives, preferentially ethyl esters of iodinated fatty acids, more preferentially ethyl esters of iodinated fatty acids of poppy oil, of olive oil, of rapeseed oil, of groundnut oil, of soybean oil or of walnut oil, and even more preferentially ethyl esters of iodinated fatty acids of poppy oil or of olive oil. More preferentially, the iodinated oil according to the invention comprises or is constituted by ethyl esters of iodinated fatty acids of poppy (also known as black poppy or *Papaver somniferum* var. *nigrum*) oil. Poppy oil, also known as poppy seed oil, preferentially contains more than 80% of unsaturated fatty acids (in particular linoleic acid (C18:2 n-6) and oleic acid (C18:1 n-9)) including at least 70% of linoleic acid and at least 10% of oleic acid. The iodinated oil is obtained from the total iodination of an oil such as poppy oil under conditions allowing one iodine atom bond for each double bond of the unsaturated fatty acids (Wolff et al. 2001, Medicine 80, 20-36) followed by transesterification.

The iodinated oil according to the invention preferentially contains from 29% to 53% (m/m) and more preferentially 37% to 39% (m/m) of iodine.

As examples of iodinated oils, mention may be made of Lipiodol®, Brassiodol® (derived from rapeseed (*Brassica compestis*) oil), Yodiol® (derived from groundnut oil), Oriodol® (derived from poppy oil in fatty acid triglyceride form) and Duroliopaque® (derived from olive oil).

Preferentially, the iodinated oil is Lipiodol®, which is an iodinated oil used as a contrast product and in certain interventional radiology procedures. This oil is a mixture of ethyl esters of iodinated and non-iodinated fatty acids of poppy seed oil. It consists predominantly (in particular more than 84%) of a mixture of ethyl esters of iodinated long-chain fatty acids (in particular C18 fatty acids) derived from poppy seed oil, preferentially as a mixture of ethyl monoiodostearate and of ethyl diiodostearate. The iodinated oil may also be an oil based on the ethyl ester of monoiodostearic acid (C18:(0) derived from olive oil. A product of this type, known as Duroliopaque®, was marketed a few years ago.

The main characteristics of Lipiodol® are the following:

| Compounds | Proportions in the fatty acid mixture |
|---|---|
| Ethyl palmitate (ethyl C16:0) | 4.6 to 6.7% (m/m), preferentially 4.8% (m/m) |
| Ethyl stearate (ethyl C18:0) | 0.8 to 1.9% (m/m), preferentially 1.2% (m/m) |
| Ethyl monoiodostearate | 11.3 to 15.3% (m/m), preferentially 13.4% (m/m) |
| Ethyl diiodostearate | 73.5 to 82.8% (m/m), preferentially 78.5% (m/m) |

| Other characteristics of Lipiodol ®: | |
|---|---|
| Iodine | 37% to 39% (m/m) (i.e. 480 mg/ml) |
| Viscosity | |
| at 37° C. | 25 mPa · s |
| at 20° C. | 50 mPa · s |
| Density | 1.268-1.290 g/cm³ at 20° C., preferentially 1.28 |

Compounds of General Formula (I)

The compounds of general formula (I) may have chiral centers and may be in racemic or enantiomeric form. The compounds of general formula (I) are included in their various forms: diastereoisomers, enantiomers or racemic mixture.

According to one embodiment, the compounds of general formula (I) are in salt form, preferably in the form of a pharmaceutically acceptable salt.

The term "pharmaceutically acceptable salt" especially denotes salts which allow the properties and the biological efficacy of the compounds according to the invention to be conserved. Examples of pharmaceutically acceptable salts are found in Berge et al., ((1977) J. Pharm. Sd, vol. 66, 1). For example, the compounds of general formula (I) are in the form of the sodium or meglumine (1-deoxy-1-(methyl-amino)-D-glucitol or N-methyl-D-glucamine) salt.

The invention also relates to the optical isomers (enantiomers), geometrical isomers (cis/trans or Z/E), tautomers and solvates such as hydrates of the compounds of formula (I).

According to one embodiment, $X_1$, $X_2$ and $X_3$ are chosen, independently of each other, from the group constituted by: H, $(C_1-C_{20})$alkyl, $(C_2-C_{20})$alkenyl and $(C_2-C_{20})$alkynyl, said alkyl, alkenyl and alkynyl groups possibly comprising one or more heteroatoms in their chain.

According to a particular embodiment, $X_1$, $X_2$ and $X_3$ are chosen, independently of each other, from the group constituted by: H and $(C_1-C_{20})$alkyl. More particularly, $X_1$, $X_2$ and $X_3$ are H.

According to one embodiment, in the compounds of general formula (I), when the radicals $Y_1$, $Y_2$ or $Y_3$ represent a group of formula (II), the corresponding radicals $R_1$ and $R_2$, $R_3$ and $R_4$ or $R_5$ and $R_6$ represent H.

According to one embodiment, the radicals $R_1$, $R_2$, $R_3$, $R_4$, $R_5$ and $R_6$ represent, independently of each other, H or a $(C_1-C_{20})$alkyl group. According to a particular embodiment, $R_1$, $R_2$, $R_3$, $R_4$, $R_5$ and $R_6$ represent H.

According to one embodiment, the radicals Ri are chosen, independently of each other, from the group constituted by: H, $(C_1-C_{20})$alkyl, $(C_2-C_{20})$alkenyl and $(C_2-C_{20})$alkynyl, said alkyl, alkenyl and alkynyl groups possibly comprising one or more heteroatoms chosen from N, O and S.

According to one embodiment, the radicals Ri are chosen, independently of each other, from the group constituted by: H, $(C_1-C_{20})$alkyl, $(C_2-C_{20})$alkenyl and $(C_2-C_{20})$alkynyl.

According to a particular embodiment, the radicals Ri are chosen, independently of each other, from the group constituted by: H and $(C_2-C_{15})$alkynyl.

According to one embodiment, the group of formula (II) is the following group:

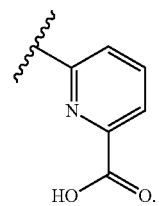 [SMILES: *c1cccc(C(=O)O)n1]

According to a particular embodiment:
$R_1$, $R_2$, $R_3$, $R_4$, $R_5$ and $R_6$ represent H; and
the radicals $Y_1$, $Y_2$ and $Y_3$ represent either a C(O)OH group or a compound having the following formula:

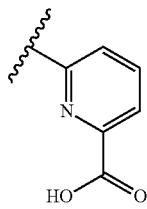

a represents the bond to the carbon atom of the group $C(R_1)(R_2)$, $C(R_3)(R_4)$ or $C(R_5)(R_6)$.

According to one embodiment, the ligand according to the invention has the general formula (I-1) below:

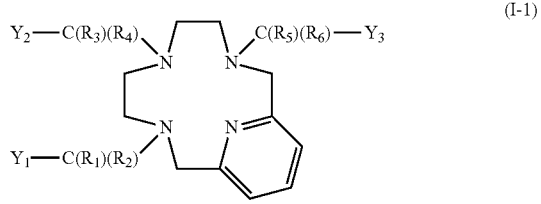

(I-1)

in which:
$R_1$, $R_2$, $R_3$, $R_4$, $R_5$ and $R_6$ represent, independently of each other, H or a $(C_1$-$C_{20})$alkyl group;
$Y_1$, $Y_2$ and $Y_3$ represent, independently of each other, a C(O)OH group or a group of formula (II) below:

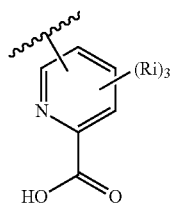

(II)

in which:
the radicals Ri are chosen, independently of each other, from the group constituted by: H, $(C_1$-$C_{20})$alkyl, $(C_2$-$C_{20})$alkenyl and $(C_2$-$C_{20})$alkynyl,
said alkyl, alkenyl and alkynyl groups possibly comprising one or more heteroatoms in their chain; and
at least one of the radicals $Y_1$, $Y_2$ and $Y_3$ being a group of formula (II);
or a pharmaceutically acceptable salt thereof.

According to one embodiment, the compounds of general formula (I) may be symmetrical or dissymmetrical. The compounds of general formula (I) are symmetrical when the groups —$C(R_1)(R_2)$—$Y_1$ and —$C(R_5)(R_6)$—$Y_3$ are identical. The compounds of general formula (I) are dissymmetrical when the groups —$C(R_1)(R_2)$—$Y_1$ and —$C(R_5)(R_6)$—$Y_3$ are different. According to one embodiment, the alkyl, alkenyl, alkynyl and aryl groups present in the radicals Ri are optionally substituted with one or more substituents, preferably one substituent, chosen from the group constituted by —COOH, —$SO_2OH$, —$P(O)(OH)_2$ and —O—$P(O)(OH)_2$; whereas the alkyl, alkenyl, alkynyl, alkylene and aryl groups of the radicals $R_1$ to $R_6$ and $X_1$ to $X_3$ are not substituted with said groups.

According to one embodiment, in the radicals $X_1$, $X_2$ and $X_3$, said alkyl, alkenyl, alkynyl and aryl groups, preferably alkyl groups, may be optionally substituted with one or more substituents, preferably one substituent, chosen from the group constituted by —COOH, —$SO_2OH$, —$P(O)(OH)_2$ and —O—$P(O)(OH)_2$.

According to one embodiment, in the radicals $R_1$, $R_2$, $R_3$, $R_4$, $R_5$ and $R_6$, the alkyl, alkylene and aryl groups, preferably alkyl groups, may be optionally substituted with one or more substituents, preferably one substituent, chosen from the group constituted by —COOH, —$SO_2OH$, —$P(O)(OH)_2$ and —O—$P(O)(OH)_2$.

According to one embodiment, in the radicals Ri, the alkyl, alkenyl, alkynyl and aryl groups, preferably alkynyl groups, may be optionally substituted with one or more substituents, preferably one substituent, chosen from the group constituted by —COOH, —$SO_2OH$, —$P(O)(OH)_2$ and —O—$P(O)(OH)_2$.

Preferably, said substituent is a —COOH group.

According to one embodiment, the compound of formula (I) is chosen from the group constituted by the following compounds:

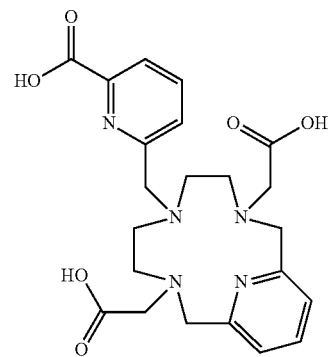

Pc-2a1pa sym

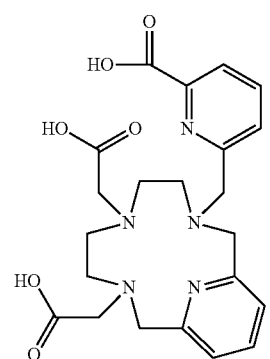

Pc-2a1pa asym

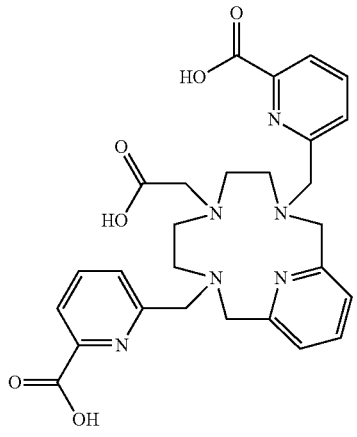

Pc-1a2pa sym

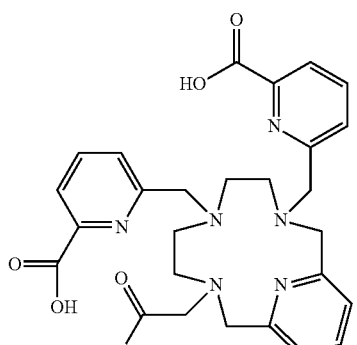

Pc-1a2pa asym

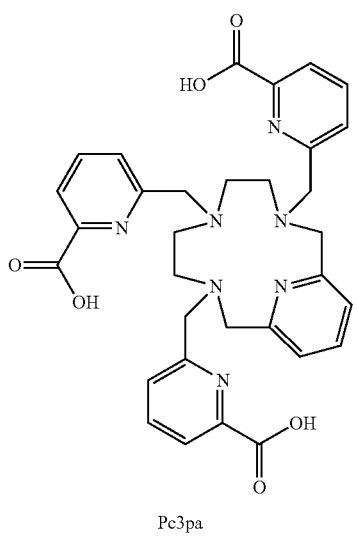

Pc3pa

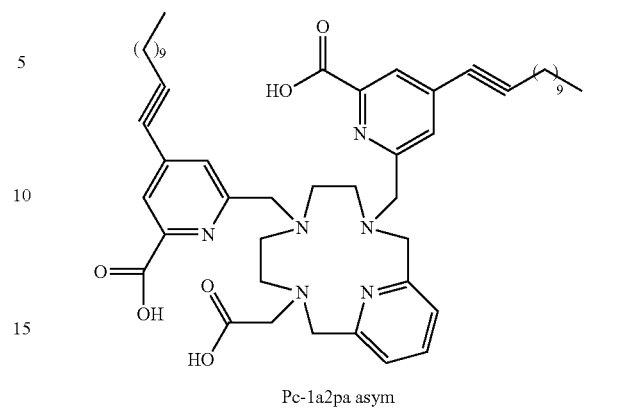

Pc-1a2pa asym

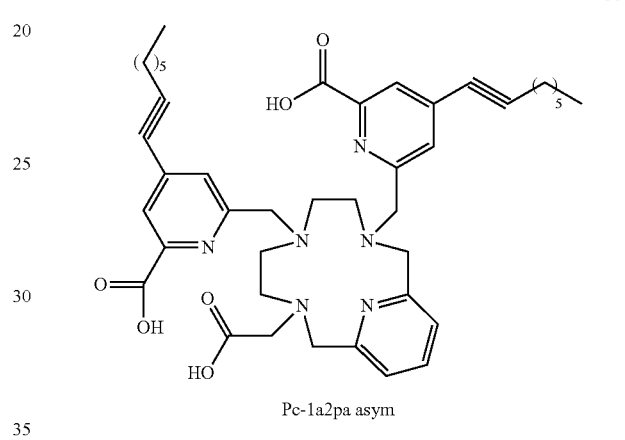

Pc-1a2pa asym or a pharmaceutically acceptable salt thereof.

According to a particular embodiment, the compound of formula (I) is the following compound:

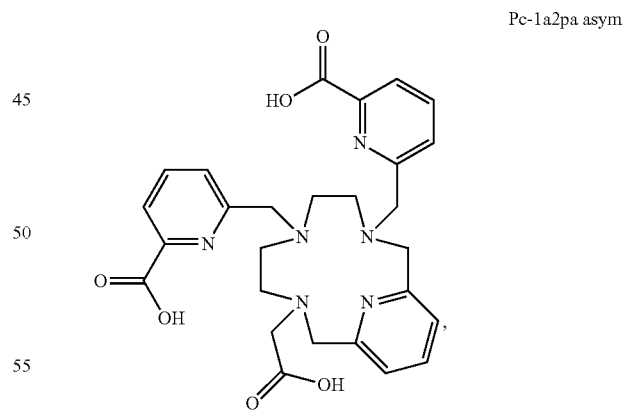

Pc-1a2pa asym or a pharmaceutically acceptable salt thereof.

Complexes

The invention also relates to a complex of a compound of formula (I) or a salt thereof, as defined above, with a chemical element M, preferably a metal.

According to one embodiment, the chemical element M is a metal cation chosen from the group constituted by bismuth (III), lead(II), copper(II), copper(I), gallium(III), zirconium (IV), technetium(III), indium(III), rhenium(VI), astatine (III), yttrium(III), samarium(III), actinium(III), lutetium (III), terbium(III), holmium(III), gadolinium(III), europium (III) and yttrium (III), preferably gadolinium(III).

According to a particular embodiment, the chemical element M is a radioelement chosen from the group constituted by $^{212}$Bi($^{212}$Pb), $^{213}$Bi(III), $^{64}$Cu(II), $^{67}$Cu(II), $^{68}$Ga(III), $^{89}$Zr(IV), $^{99m}$Tc(III), $^{111}$In(III), $^{186}$Re(VI), $^{188}$Re(VI), $^{211}$At (III), $^{225}$Ac(III), $^{153}$Sm(III), $^{149}$Tb(III), $^{166}$Ho(III), $^{212}$Bi ($^{212}$Pb), $^{213}$Bi(III), preferably $^{177}$Lu(III), $^{90}$Y(III) and $^{166}$Ho (III). Preferably, M is a radioelement chosen from the yttrium and lanthanide radioactive isotopes.

In particular, among the radioelements according to the invention, mention may be made of: $^{177}$Lu, $^{149}$Tb, $^{152}$Tb, $^{155}$Tb, $^{161}$Tb, $^{86}$Y and $^{153}$Sm. According to a particular embodiment, M is a radioelement chosen from the group constituted by $^{166}$Ho, $^{177}$Lu and $^{90}$Y.

According to one embodiment, said complex is of general formula (III) below:

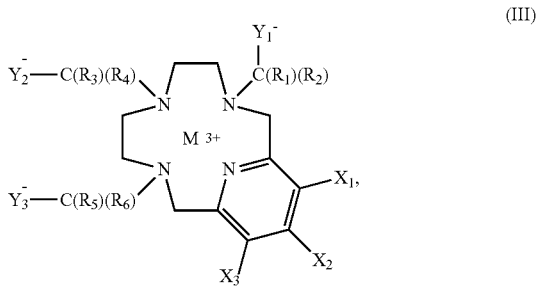

(III)

in which $R_1$, $R_2$, $R_3$, $R_4$, $R_5$, $R_6$, $X_1$, $X_2$, $X_3$, $Y_1$, $Y_2$, $Y_3$ and M are as defined above. In particular, in the general formula (III), each of the groups $Y_1$, $Y_2$ and $Y_3$ comprises a C(O)O$^-$ group, which allows complexing with the element M.

Pharmaceutical Composition

The invention also relates to a pharmaceutical composition comprising a compound of formula (I) as defined above or complex as defined above, and optionally one or more pharmaceutically acceptable excipients.

The composition may also comprise a buffer chosen from the buffers of established use, for instance lactate, tartrate malate, maleate, succinate, ascorbate, carbonate, tris((hydroxymethyl)aminomethane), HEPES (2-[4-(2-hydroxyethyl)-1-piperazine]ethanesulfonic acid) or MES (2-morpholinoethanesulfonic acid) buffers, and mixtures thereof.

The pharmaceutical composition may comprise an oily phase, especially an iodinated oil. According to a particular embodiment, the pharmaceutical composition also comprises ethyl esters of iodinated fatty acids of poppy oil.

According to one embodiment, the pharmaceutical composition according to the invention is constituted by an iodinated oil and complexes according to the invention. Typically, the pharmaceutical composition according to the invention is constituted by Lipiodol® and complexes according to the invention. Lipiodol® is constituted by ethyl esters of iodinated fatty acids of poppy oil.

Preferably, the pharmaceutical composition according to the invention is radioopaque, and thus visible by x-ray radiography.

According to a particular embodiment, the pharmaceutical composition is an injectable composition. According to one embodiment, the pharmaceutical composition according to the invention is administered by intra-arterial hepatic injection.

The invention relates to a complex or a pharmaceutical composition as defined above, for its use in the treatment of cancer.

The invention also relates to a complex or a pharmaceutical composition as defined above, for its use in medical imaging.

The invention relates to the use of a complex as defined above for the preparation of a medicament for treating cancer.

The invention also relates to the use of a complex or a pharmaceutical composition as defined above in medical imaging.

The invention relates to a method for the therapeutic treatment of a patient suffering from cancer, comprising the administration to said patient of a complex or a pharmaceutical composition as defined above. In particular, said treatment method does not comprise a step of surgical treatment.

The invention also relates to a method for the medical imaging of a tumor, comprising:
  a step of administering to a patient suffering from cancer a complex or a pharmaceutical composition according to the invention; and
  a step of detecting the tumor via a medical imaging method.

The term "cancer" refers to an abnormal cell proliferation (also known as a tumor) in a normal tissue of the body. These cancer cells all derive from the same clone, a cell initiating the cancer, which has acquired certain characteristics enabling it to divide indefinitely. In the course of evolution of the tumor, certain cancer cells may migrate from their site of production and form metastases.

Among cancers, mention may be made especially of liver cancer, in particular primary liver cancer, preferably hepatocarcinoma. According to a particular embodiment, among cancers, mention may be made of hepatocarcinoma, epitheloid hemangioendothelioma, cholangiocarcinoma, neuroendocrine tumors and metastases of other cancers such as colorectal cancer metastases.

According to a particular embodiment, the cancer is an intermediate-stage hepatocellular carcinoma, in adults.

Process for Preparing the Compounds of General Formula (I) and Radiolabeling

The compounds of general formula (I) may be prepared according to two processes, depending on whether the compounds of general formula (I) are symmetrical or dissymmetrical.

In these preparation processes, the deprotection steps are known to those skilled in the art and correspond to standard reactions of hydrolysis of an amide. The functionalization steps are also known to those skilled in the art and correspond to standard alkylation reactions (cf. Loic Bellouard *J CHEM S Perkin* 1, (23), 1999, pages 3499-3505).

The first applicable approach for symmetrical compounds involves the total synthesis of the pyclene macrocycle with the need to differentiate the central nitrogen atom (6) from the nitrogen atoms in the side positions (3 and 9).

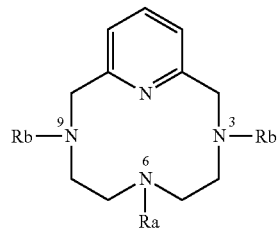

To do this, the method proposed by Siauge et al. is applicable (Tetrahedron, volume 57, issue 22, pages 4713-4718). This method is based, firstly, on the use of a nosyl (2-nitrophenylsulfonyl) group instead of the tosyl groups usually chosen to perform macrocyclizations according to the general method of Richman and Atkins (J. Am. Chem. Soc. 1974, 96, 2268-2270) and on the selective reactivity of primary amines of diethylenetriamine. According to this principle, it is possible to prepare diethylenetriamine-based intermediates that are variously substituted on the central secondary amine (prefiguring the substitution in position 6). These compounds are key intermediates which can then be employed in the macrocyclization reaction. The presence of nosyl groups, which are easier to deprotect than the tosyl analogs, allows the introduction onto the macrocycle of a wider diversity of substituents in position 6. Scheme 1 below illustrates this preparation process.

—C($R_3$)($R_4$)—$Y_2$, with $R_3$, $R_4$ and $Y_2$ as defined for the compounds of general formula (I), an ester or an orthogonal protecting group such as tert-butoxycarbonyl and Z is a leaving group such as Cl, Br, I, tosylate mesylate or triflate. This preparation process is referred to as the "Direct route" or "Boc route" in the examples.

The invention also relates to a process for preparing the compounds of general formula (I) according to the invention which are dissymmetrical. This preparation process is advantageously based on the reaction of an oxalic acid diester with pyclene, which makes it possible to block two nitrogen atoms of pyclene (N-6 and N-9) so as to be able to act selectively on the third atom (N-3) which has remained free. After functionalization of the nitrogen in position -3, deprotection of the oxalamide group leads to a pyclene

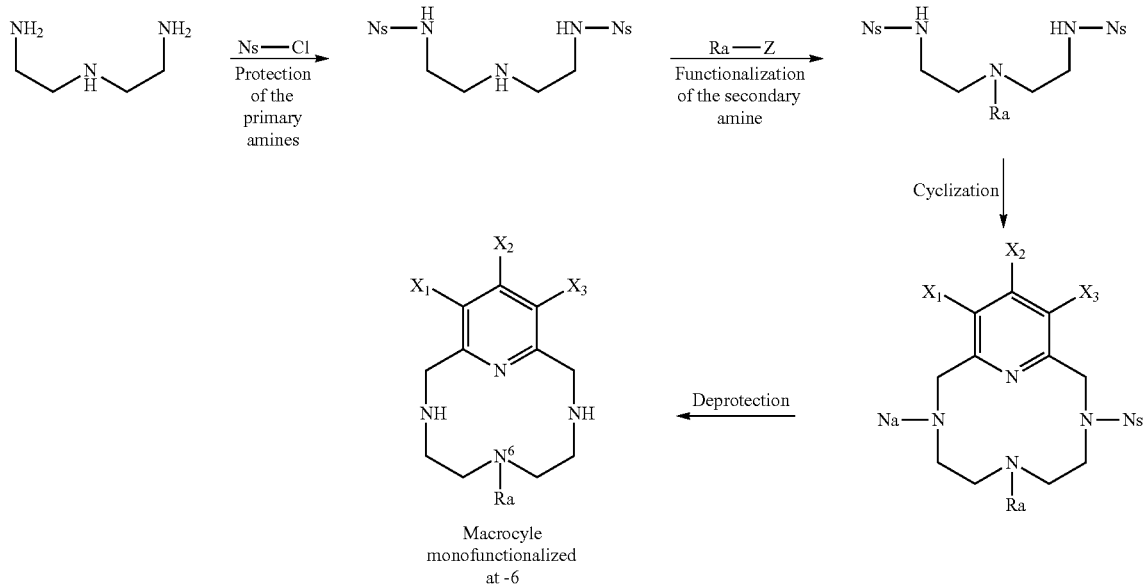

Scheme 1

Macrocycle monofunctionalized at -6

In scheme 1, $X_1$, $X_2$ and $X_3$ are as defined for the compounds of general formula (I), the group Ra is a group which is substituted in position -3 in a controlled manner, according to scheme 2 below:

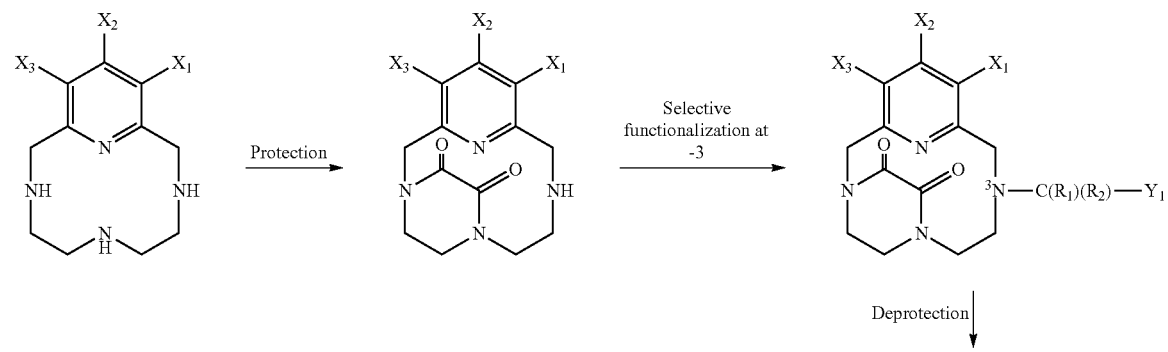

Scheme 2

-continued

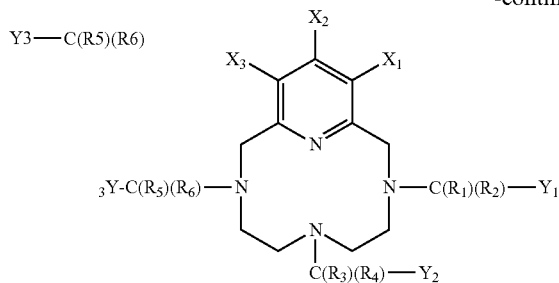
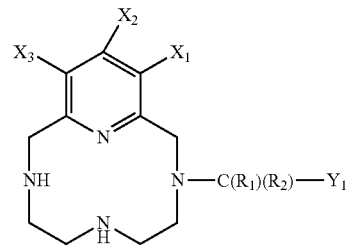

Functionalization

In scheme 2, $X_1$, $X_2$, $X_3$, $R_1$ to $R_6$ and $Y_1$ to $Y_3$ are as defined for the compounds of general formula (I). According to one embodiment, the protection step is performed in the presence of methanol.

The invention relates to a process for preparing the compounds of general formula (I) for which the groups —$C(R_1)(R_2)$—$Y_1$ and —$C(R_5)(R_6)$—$Y_3$ are different, comprising a step of functionalizing a compound of general formula (IX) below:

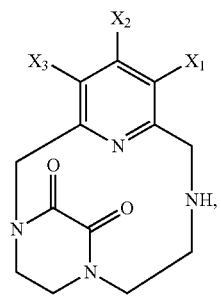

to form a compound of general formula (X) below:

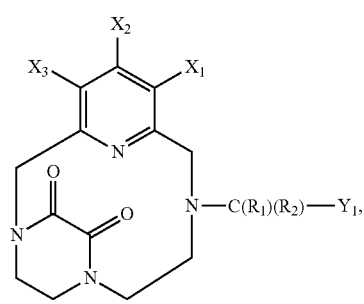

in which $X_1$, $X_2$, $X_3$, $R_1$, $R_2$ and $Y_1$ are as defined for the compounds of general formula (I).

According to a particular embodiment, said preparation process also comprises:

a step of deprotection of the compound of general formula (X) to obtain a compound of general formula (XI) below:

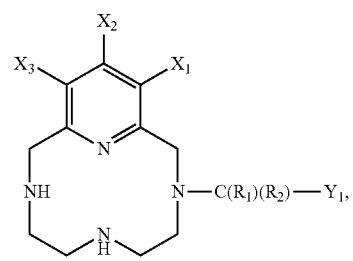

in which $X_1$, $X_2$, $X_3$, $R_1$, $R_2$ and $Y_1$ are as defined for the compounds of general formula (I), and a step of functionalization of the compound of general formula (XI) to obtain a compound of general formula (I) as defined above.

The term "functionalization" means the addition to a nitrogen atom of a group —$C(R_1)(R_2)$—$Y_1$, —$C(R_3)(R_4)$—$Y_2$ or —$C(R_5)(R_6)$—$Y_3$.

The invention also relates to a compound of general formula (X) below:

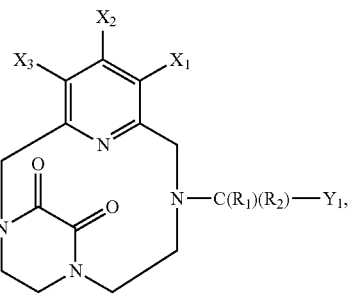

(X)

in which $X_1$, $X_2$, $X_3$, $R_1$, $R_2$ and $Y_1$ are as defined for the compounds of general formula (I).

According to a particular embodiment of the process for preparing the dissymmetrical compounds of formula (I), when at least one of the Ri is other than H, the preparation of a substituted picolinate intermediate is performed via a bromo derivative in position -4, which makes it possible, via a palladium-catalyzed coupling reaction with an alkyne (Sonogashira reaction, Comprehensive Chirality, volume 4, pages 18-32, 2012), to install the chosen residue, according to scheme 3 below (example with a $C_{12}$ alkyne):

Scheme 3

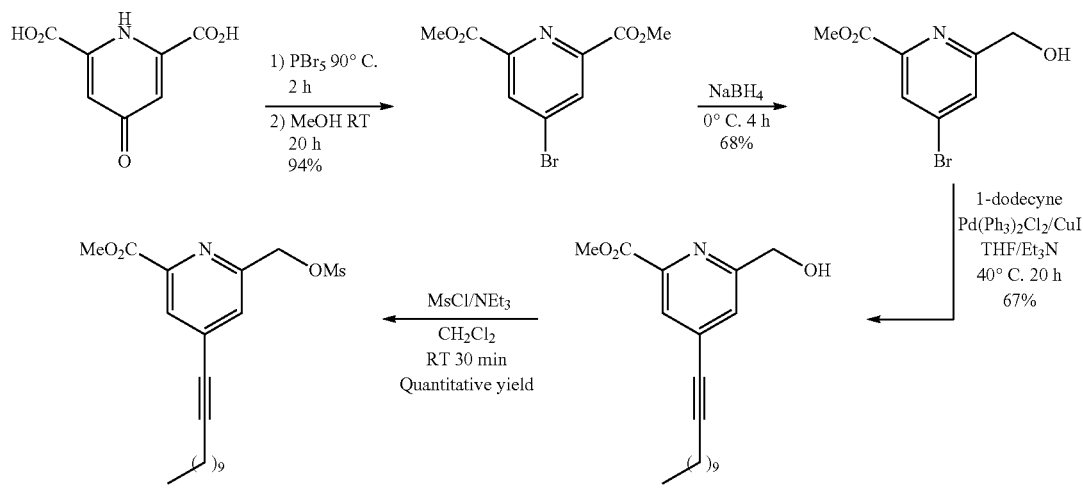

The invention also relates to a process for radiolabeling the compounds of general formula (I), said radiolabeling process preferably being performed at a pH of between 6.5 and 9. According to a particular embodiment, said radiolabeling is performed in the presence of acetate buffer. According to one embodiment, the radiolabeling is performed in the presence of water or of an alcohol such as ethanol, or mixtures thereof.

According to another embodiment, the radiolabeling is performed at a temperature of between 80° C. and 100° C.

Figure 1:
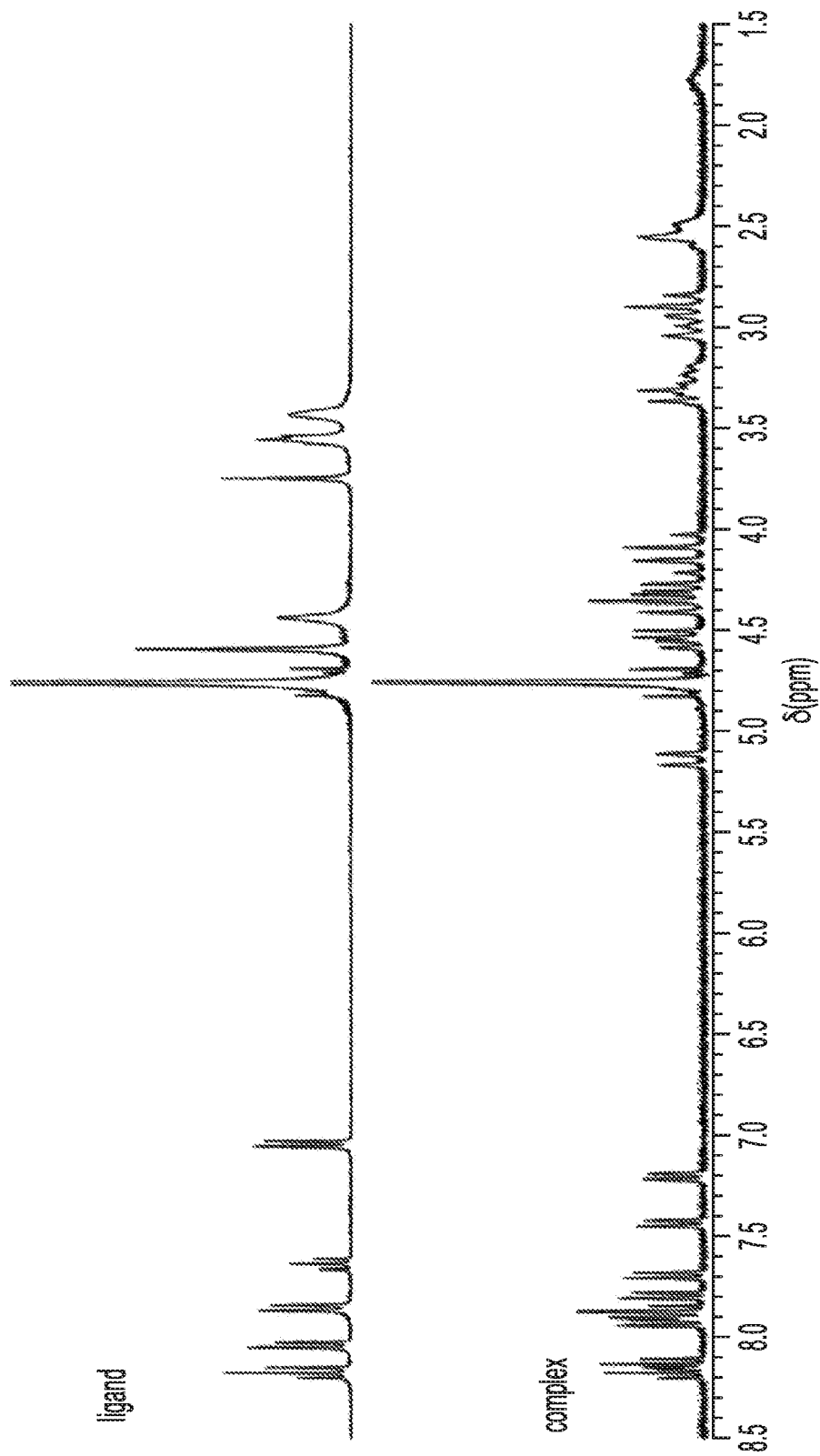
FIG. 1: $^1$H NMR spectra of the ligand P04213 and of its yttrium complex P04183 (300 MHz, 298 K, D$_2$O)

The examples that follow are described as illustrations of the present invention.

EXAMPLES

Summary table of the various names of the specific compounds of general formula (I) according to the invention:

| | Abbreviation | Ligand | Yttrium complex | $^{90}$Yttrium complex |
|---|---|---|---|---|
| Mono S | Pc-2a1pa Sym | P04218 | P04219 | |
| Mono AS | Pc-2a1pa Asym | P04216 | P04217 | |

-continued

| | Abbreviation | Ligand | Yttrium complex | $^{90}$Yttrium complex |
|---|---|---|---|---|
| Di Sym | Pc-1a2pa sym | P04213 | P04183 | |
| Di AS | Pc-1a2pa Asym | P04214 | P04215 | P04233 |
| Tri | Pc-3pa | P04221 | P04222 | |
| Di AS | Pc-1a2pa Asym C12 | P04245 | | P04283 |
| Di AS | Pc-1a2pa Asym C8 | P04330 | | |

A—Materials and Methods

Yttrium-90 chloride is purchased from PerkinElmer Life Sciences. The activities involved were between 28 μCi and 8.51 mCi (1.04-314.87 MBq). The products (HPLC solvents, buffers, etc.) are used as furnished, without further purification. Unless otherwise specified, the ligand is dissolved in ethanol.

The experiments were performed in crimped borosilicate glass bottles. The bottles were heated in a Bioblock heating block allowing up to 6 bottles to be heated. When stirring was necessary, a Lab Dancer S40 (VWR) vortex machine was used. The centrifugations were performed with an MF 20-R centrifuge (Awel).

The activities were measured in a CRC-127R activimeter (Capintec), which was calibrated each morning.

The quality controls were performed by TLC on Whatman 1 paper with an MeOH/0.1% Et$_3$N mixture as eluent. The radiochemical purities are determined using a Cyclone phosphoimager (Perkin Elmer), with the aid of the Optiquant software.

HPLC analyses were also performed, on a Dionex Ultimate 3000 HPLC line equipped with a diode array detector and an fLumo radiochromatographic detector (Berthold), run by the Chromeleon software.

The analyses were performed on an Accucore C18 100×3 mm, 2.6μ column with the following program: 0.4 mL/min; A=H$_2$O; B=ACN; 0-3 min: 100% A; 3-20 min: 0-90% B; 20-25 min: 10% A/90% B; 25-26 min: 90-0% B; 26-30 min: 100% A.

Spectroscopic Studies

The UV-visible spectra of the ligands and of the yttrium(III) complexes were measured in aqueous solution of acetate buffer (pH=5.5 or 3.8 without control of the ionic strength) at 298 K using a Jasco V-650 spectrophotometer.

The NMR experiments (COSY, HMBC and HMQC) were recorded for the ligands and their complexes using a Brüker Avance 500 spectrometer (500 MHz) in $D_2O$.

Kinetic Studies

The formation of the yttrium(III) complexes of do2pa sym, do2pa asym and do1pa sym were studied in an aqueous solution of acetate buffer (C=0.150 M) at 25° C. under pseudo-first-order conditions. The increase in intensity of the absorption band in the UV region was monitored at pH=3.8 and 5.5 with $C_L=C_M=4\times10^{-5}$ M and without control of the ionic strength.

Dissociation in acidic medium of the yttrium(III) complexes was studied under pseudo-first-order conditions without control of the ionic strength and by addition of aqueous solutions of HCl (0.5, 1, 2, 4 and 5M) to a solution of complex (C=$4.10^{-5}$ M).

The dissociation was monitored by decrease of the intensity of the absorption band of the complex or increase of the absorption band of the ligand in the UV region. $t_{1/2}$ was calculated by adjusting the curve $A_{max}=f(t)$ ($A_{max}$=absorbance at $\lambda_{max}$ of the complex or of the ligand) with the following pseudo-first-order exponential equation: Abs(t)=Abs(eq)+(Abs(0)−Abs(eq))×exp (−x/t1).

Potentiometric Studies

Equipment:

The experiments were performed under an inert atmosphere in aqueous solutions thermostatically maintained at 25.0±0.1° C. The protonation and complexation titrations were performed in a jacketed glass titrations cell using a Metrohm 702 SM Titrino automatic burette connected to a Metrohm 6.0233.100 combined glass electrode. The titrations were controlled automatically by software after selection of the appropriate parameters avoiding monitoring during long measurements.

The titrant is an approximately 0.1 M KOH solution prepared from an analytical-grade commercial vial and its exact concentration is obtained by applying the Gran method by titrating with a standard $HNO_3$ solution.

The ligand solutions were prepared at approximately 2.0×$10^{-3}$ M and the $Cu^{2+}$, $Pb^{2+}$ and $Y^{3+}$ solutions at approximately 0.04 M from analytical-grade chloride salts and standardized by complexometric titration with $H_4$edta (ethylenediaminetetraacetic acid)[1]. The solution to be titrated contains approximately 0.05 mmol of ligand in a volume of 30.00 mL, the ionic strength of which was maintained at 0.10 M using $KNO_3$ as electrolyte. 1.2 equivalents of metal cation ($Cu^{2+}$ or $Pb^{2+}$) were added to the ligand (0.05 mmol) during the standardization titrations of the ligand solution. 0.9 equivalent of metal cation ($Y^{3+}$) was added to the ligand during the complexation titration methods.

Measurements

The electromotive force of the solution was measured after calibration of the electrode by titration of a standard $2.10^{-3}$ M $HNO_3$ solution. The [$H^+$] of the solutions was determined by measuring the electromotive force of the cell, E=E°'+Q log [$H^+$]+Ej. The term "pH" is defined by −log [$H^+$]. E°' and Q are determined by the acidic region of the calibration curves. The liquid junction potential, Ej, is negligible under the experimental conditions used. The value of $K_e$=[$H^+$][$OH^-$] is $10^{-13.78}$.

Calculations

The potentiometric data were refined with the Hyperquad software[2] and the speciation diagrams were plotted using the HySS software[3].

The overall equilibrium constants $\beta_rH$ and $\beta M_mH_hL_l$ are defined by $\beta M_mH_hL_l=[M_mH_hL_l]/[M]_m[H]_h[L]_l$ ($\beta_rH=[H_hL_l]/[H]_h[L]_l$ and $\beta MH_{-1}L=\beta ML(OH)\times Ke$). The differences, in log units, between the protonation (or hydrolysis) values and the non-protonation constants give the intermediate reaction constants (log K) (with $KM_mH_hL_l=[M_mH_hL_l]/[M_mH_{h-1}L_l]$[H]). The errors indicated are the standard deviations calculated by the adjustment program from all of the experimental data for each system.

B— Synthesis of the Compounds of General Formula (I)

All the commercial reagents were used as received from the suppliers, unless otherwise indicated. The solvents were distilled before use, according to the procedures described in the literature. The purifications by semi-prep HPLC (high-performance liquid chromatography) were performed with a Prominence Shimadzu HPLC/LCMS-2020 machine equipped with an SPD-20 A UV detector. The HPLC chromatographic system uses a column (VisionHT $C_{18}$ HL 5µ250×10 mm) eluted with an $H_2O$ (with 0.1% TFA or HCl)-MeCN isocratic gradient.

The $^1H$ and $^{13}C$ NMR spectra were recorded on a Brüker AMX3-300 MHz spectrometer operating at 300.17 and 75.47 MHz, respectively, for $^1H$ and $^{13}C$. All the measurements were taken at 25° C. The signals are indicated as follows: δ chemical shift (ppm), multiplicity (s, singlet; d, doublet; t, triplet; m, multiplet; q, quartet), integration, coupling constants J in hertz (Hz).

The high-resolution mass spectrometry (HRMS-ESI) was performed in positive electrospray ionization mode (ESI+) by the mass spectrometry department of the Institut de Chimie Organique et Analytique (ICOA), Orleans, France.

1) Synthesis of the Ligands Pc1a2pa Sym P04213 of Formula (I) Via the "Direct" Route Synthetic scheme of example 1

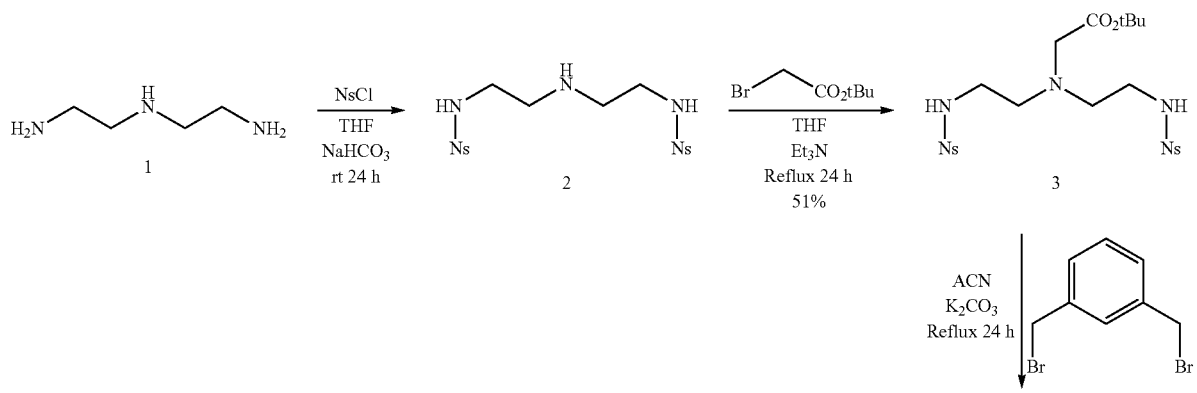

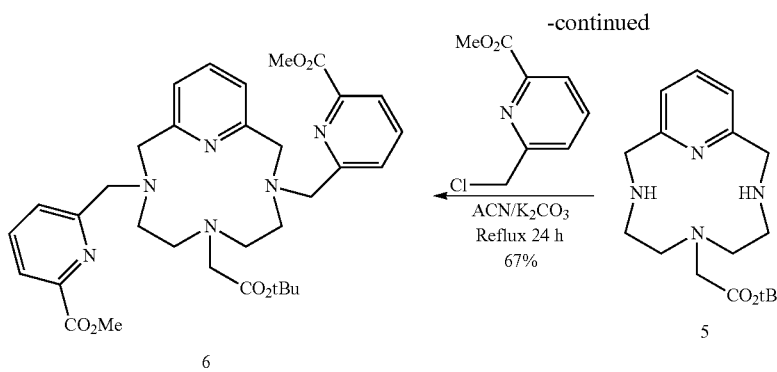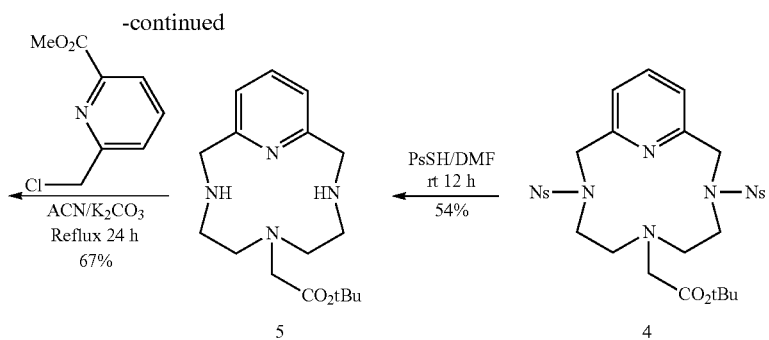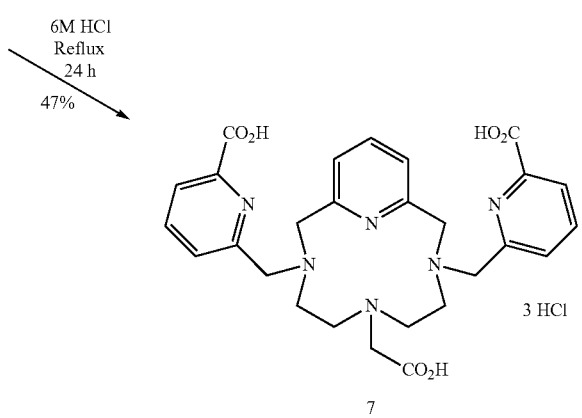

Example 1—Int.2

A solution of 2-nitrobenzenesulfonyl chloride (4.3 g, 19.4 mmol) in freshly distilled THF is added at 0° C. to a mixture of diethylenetriamine (1.0 g, 9.69 mmol) and NaHCO$_3$ (3.26 g, 38.8 mmol) in THF (200 ml). The medium is stirred at room temperature for 20 hours and the solid is then filtered off. The filtrate is concentrated to dryness to give a white solid. This compound is used in the following reaction without purification.

$^1$H NMR (300 MHz, DMSO-d$_6$): δ 8.03-7.82 (m, 8H), 2.87 (t, 4H, $^3$J=6.0 Hz), 2.47 (t, 4H, $^3$J=6.0 Hz).

$^{13}$C NMR (75.47 MHz, DMSO-d$_6$): δ 147.73, 133.99, 132.68, 132.60, 129.49, 124.39, 47.80, 42.65.

Example 1—Int.3

A solution of tert-butyl bromoacetate (6.09 g, 31.2 mmol) in THF (50 ml) is added to a solution of the compound prepared previously (4.93 g, 10.4 mmol) and of triethylamine (6.31 g, 62.4 mmol) in THF (75 ml). The mixture is refluxed for 24 hours. After cooling the medium, 50 ml of saturated NH$_4$Cl solution are added and the solvent is removed by evaporation under reduced pressure. The aqueous phase thus obtained is extracted three times with 50 ml of CH$_2$Cl$_2$. The chloromethylene fractions are combined and dried over MgSO$_4$ and then filtered. After evaporating off the solvent, the white solid obtained is chromatographed on silica gel (5/5 to 8/2 ethyl acetate/pentane) to give a white solid after evaporating off the solvent (2.9 g, 51% calc. starting from 1).

$^1$H NMR (300 MHz, CDCl$_3$): δ 8.09 (m, 2H), 7.82 (m, 2H), 7.72 (m, 4H), 5.94 (t, 2H, $^3$J=5.7 Hz), 3.17 (s, 2H), 3.07 (m, 4H), 2.76 (t, 4H, $^3$J=5.7 Hz), 1.41 (s, 9H).

$^{13}$C NMR (75.47 MHz, CDCl$_3$): δ 170.78, 148.27, 133.71, 133.45, 132.78, 130.97, 125.52, 82.13, 55.99, 54.65, 41.90, 28.16.

Example 1—Int.4

4 g of K$_2$CO$_3$ are added to a solution in acetonitrile (20 ml) of the compound prepared previously (2.86 g, 4.87 mmol) and the mixture is brought to reflux. Dibromomethylpyridine (1.55 g, 5.84 mmol) dissolved in 10 ml of acetonitrile is then added. The medium is refluxed overnight and the solid is filtered off after cooling. The solvent is evaporated off under reduced pressure. The compound obtained is used in the following reaction without further purification.

$^1$H NMR (300 MHz, CDCl$_3$): δ 8.1-7.6 (m, 9H), 7.42 (d, 2H, $^3$J=7.8 Hz), 4.56 (s, 4H), 3.30 (m, 4H), 3.17 (s, 2H), 2.57 (m, 4H), 1.37 (s, 9H).

$^{13}$C NMR (75.47 MHz, CDCl$_3$): δ 171.09, 154.75, 148.33, 139.17, 133.81, 132.74, 131.91, 130.86, 124.39, 124.27, 81.25, 57.51, 54.33, 51.18, 44.93, 28.18.

Example 1—Int.5

The compound prepared previously (2.9 g, 4.29 mmol) is dissolved in DMF in the presence of Na$_2$CO$_3$ (3.64 g, 34.3 mmol). Thiophenol (1.88 g, 17.2 mmol) is then added and the medium is stirred at room temperature overnight. After evaporating off the solvent, the residue is taken up in CH$_2$Cl$_2$ (100 ml) and the solution obtained is washed with 3×40 ml of 0.5 M NaOH solution. After drying over MgSO$_4$ and filtration, the organic solution is concentrated and the product obtained is chromatographed on neutral alumina (99/1 CH$_2$Cl$_2$/MeOH) to give a white solid (0.835 g, 54% calc. starting from 3).

¹H NMR (300 MHz, CDCl₃): δ 7.4 (t, 1H, ³J=7.5 Hz), 6.86 (d, 2H, ³J=7.5 Hz), 3.83 (s, 4H), 3.22 (s, 2H), 2.48 (m, 4H), 2.40 (m, 4H), 1.28 (s, 9H).
¹³C NMR (75.47 MHz, CDCl₃): δ 171.06, 157.49, 136.65, 120.03, 80.98, 59.10, 56.00, 52.67, 47.41, 27.95.

Example 1—Int.6

The methyl ester of 6-chloromethyl-2-pyridinecarboxylic acid (0.872 g, 4.70 mmol) is added to a solution of the compound prepared previously (0.835 g, 2.61 mmol) in acetonitrile (35 ml) in the presence of K₂CO₃ (1.4 g, 10.4 mmol). The medium is refluxed overnight and then filtered and concentrated. The residue is purified by chromatography on neutral alumina (98/2 CH₂Cl₂/MeOH) to give 1.09 g of a yellow oil (67%).
¹³C NMR (75.47 MHz, CDCl₃): δ 169.95, 164.98, 158.48, 145.96, 138.30, 137.54, 126.69, 123.11, 119.93, 81.07, 62.45, 61.81, 54.44, 53.13, 52.18, 51.19, 27.51.

Example 1—Int.7

The compound prepared previously (1.09 g, 1.76 mmol) is dissolved in 6M hydrochloric acid solution and the medium is refluxed overnight. After concentration, the product is purified by HPLC on a C₁₈ phase (100/0 to 10/90 H₂O/acetonitrile) to give intermediate 7 in hydrochloride form (0.690 g, 57% calc. for 3 HCl).

¹H NMR (500.25 MHz, D₂O): δ 8.21 (t, 2H, ³J=7.8 Hz), 8.07 (d, 2H, ³J=7.8 Hz), 7.88 (d, 2H, ³J=7.8 Hz), 7.68 (t, 1H, ³J=7.8 Hz), 7.07 (d, 2H, ³J=7.8 Hz), 4.63 (s, 4H), 4.45 (s, br, 4H), 3.78 (s, 2H), 3.58 (m, 4H), 3.46 (s, br, 4H).
¹³C NMR (125.79 MHz, D₂O): δ 175.11, 170.44, 157.33, 153.78, 152.13, 145.76, 142.12, 131.02, 127.79, 124.63, 62.55, 60.72, 57.63, 56.20, 54.67.

2) Synthesis of Pc2a1pa Sym P04218 of Formula (I) Via the "Direct" Route

Synthetic scheme of example 2

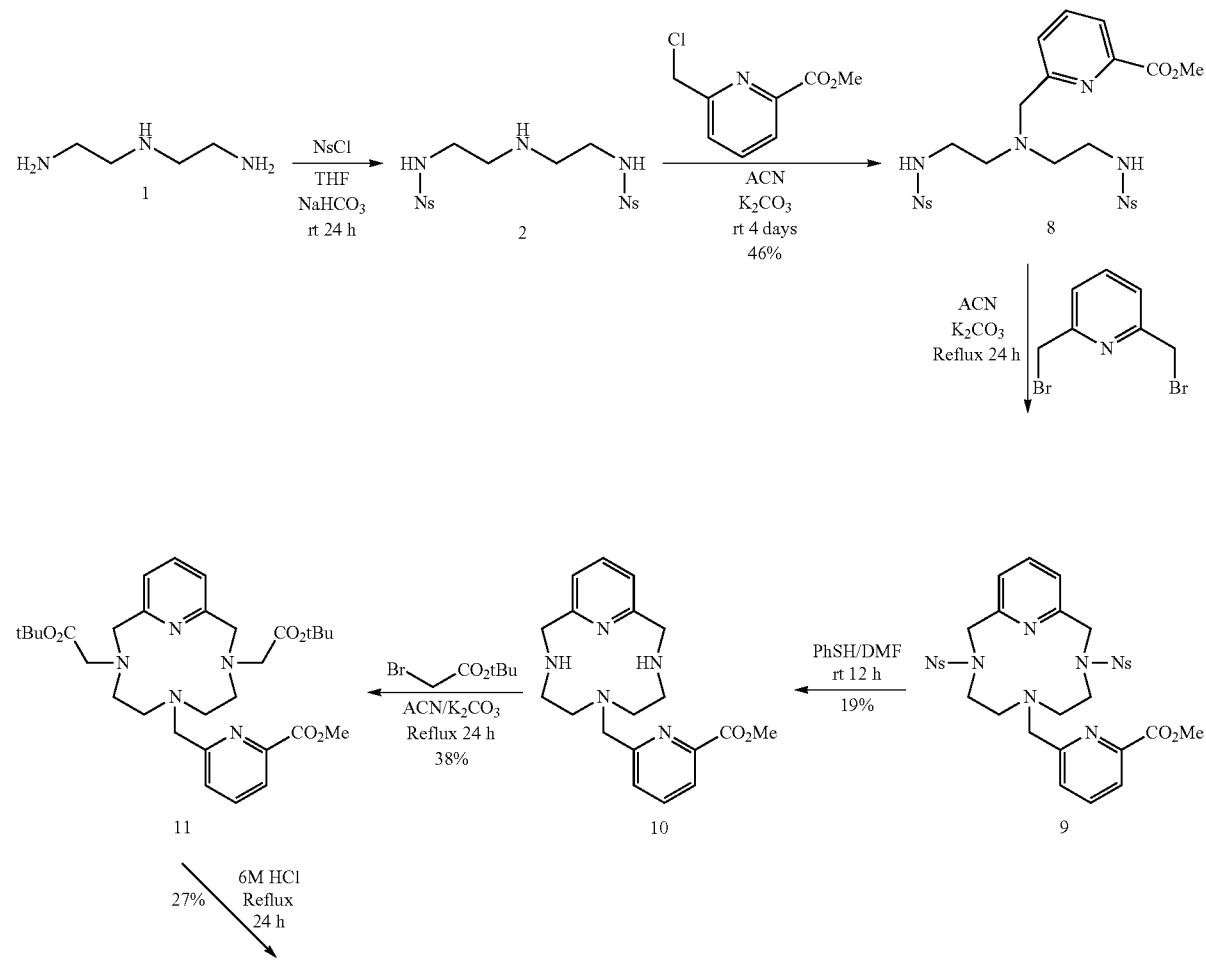

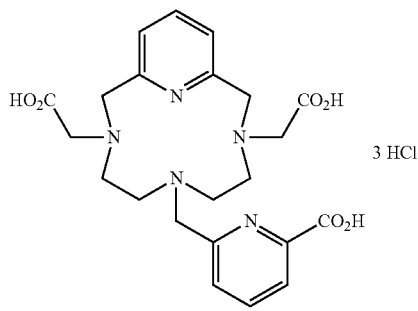

12

Example 2—Int.8

The methyl ester of 6-chloromethyl-2-pyridinecarboxylic acid (1.93 g, 10.42 mmol) is added to a solution of compound 2 (Example 1-int.2) (4.935 g, 10.42 mmol) in acetonitrile (60 ml) in the presence of $K_2CO_3$ (4.3 g, 31.26 mmol) and the mixture is stirred at room temperature for 4 days. The solvent is evaporated off and the residue is taken up in $CH_2Cl_2$, filtered, concentrated and purified by chromatography on silica gel (5/5 to 8/2 ethyl acetate/pentane). The product is recovered in the form of a yellow oil (2.78 g, 46% calc. starting from 1).

$^1$H NMR (300 MHz, $CDCl_3$): δ 8.08-7.99 (m, 2H), 7.95 (d, 1H, $^3J$=7.9 Hz), 7.82-7.61 (m, 7H), 7.47 (d, 1H, $^3J$=7.9 Hz), 6.21 (m, 2H), 3.94 (s, 3H), 3.78 (s, 2H), 3.10 (m, 4H), 2.68 (t, 4H, $^3J$=5.5 Hz).

$^{13}$C NMR (75.47 MHz, $CDCl_3$): δ 165.64, 159.19, 148.11, 147.80, 138.01, 133.58, 132.71, 130.71, 126.16, 125.18, 123.99, 59.45, 54.83, 53.03, 41.58.

Example 2—Int.9

The compound prepared previously (2.78 g, 4.46 mmol) and 3.7 g of $K_2CO_3$ in 30 ml of acetonitrile are brought to reflux and a solution of dibromomethylpyridine (1.42 g, 5.36 mmol) in 10 ml of acetonitrile is then added. The medium is stirred at the reflux point of the acetonitrile overnight, the solid is then filtered off and the filtrate is concentrated under reduced pressure. The compound obtained is used in the following step without further purification.

$^1$H NMR (300 MHz, $CDCl_3$): δ 7.88-7.50 (m, 12H), 7.35 (d, 2H, $^3J$=7.5 Hz), 4.52 (s, 4H), 3.89 (s, 3H), 3.77 (s, 2H), 3.27 (m, 4H), 2.52 (m, 4H).

$^{13}$C NMR (75.47 MHz, $CDCl_3$): δ 165.23, 159.52, 153.98, 147.55, 146.63, 138.66, 137.10, 133.39, 131.81, 131.45, 130.08, 125.18, 123.78, 123.57, 123.25, 120.99, 120.56, 59.82, 53.62, 52.33, 48.61, 43.35.

Example 2—Int.10

The compound prepared previously (3.9 g, 5.5 mmol) is dissolved in DMF in the presence of $Na_2CO_3$ (4.6 g, 43.9 mmol), thiophenol (2.42 g, 21.9 mmol) is then added and the medium is stirred at room temperature overnight. The solvent is then removed by distillation under reduced pressure and the residue is taken up in 100 ml of $CH_2Cl_2$. After washing the organic phase 3 times (3×40 ml) with 0.5M sodium hydroxide solution, drying over $MgSO_4$ and evaporation of the solvent, the residue obtained is purified by chromatography on neutral alumina (99/1 $CH_2Cl_2$/MeOH) to give a yellow oil (0.297 g, 19% calc. starting from 8).

$^1$H NMR (300 MHz, $CDCl_3$): δ 7.93 (d, 1H, $^3J$=7.5 Hz), 7.76 (t, 1H, $^3J$=7.5 Hz), 7.61 (t, 1H, $^3J$=7.5 Hz), 7.40 (d, 1H, $^3J$=7.5 Hz), 7.07 (d, 2H, $^3J$=7.5 Hz), 4.13 (s, 4H), 4.00 (s, 2H), 3.79 (s, 3H), 2.73 (m, 8H).

$^{13}$C NMR (75.47 MHz, $CDCl_3$): δ 165.32, 159.60, 155.26, 147.50, 137.96, 137.52, 125.85, 123.96, 120.60, 61.47, 55.96, 52.67, 51.96, 47.09.

Example 2—Int.11

To a mixture of tert-butyl bromoacetate (0.294 g, 1.50 mmol) and $K_2CO_3$ (0.464 g, 3.4 mmol) in 10 ml of acetonitrile is added the compound prepared previously (0.297 g, 0.84 mmol). The medium is refluxed overnight, the solid is then filtered off and the solution obtained is concentrated. The residue obtained is purified by chromatography on neutral alumina (100/0 to 95/5 $CH_2Cl_2$/MeOH) to give compound 11 in the form of a yellow oil (0.185 g, 38%).

Example 2—Int.12

The compound prepared previously (0.185 g, 0.32 mmol) is dissolved in 20 ml of 6M HCl and the medium is refluxed overnight. After evaporating off the solvent, the product is purified by HPLC on a C18 phase (100/0 to 10/90 $H_2O$/acetonitrile) to give the expected product in hydrochloride form (0.050 g, 27% calc. for 3 HCl).

$^1$H NMR (500.25 MHz, $D_2O$): δ 8.33 (t, 1H, $^3J$=7.8 Hz), 8.25 (d, 1H, $^3J$=7.8 Hz), 8.07 (d, 1H, $^3J$=7.8 Hz), 8.00 (t, 1H, $^3J$=7.8 Hz), 7.49 (d, 2H, $^3J$=7.8 Hz), 4.81 (s, 4H), 4.20 (s, 2H), 3.76 (s, 4H), 3.63 (m, 4H), 2.99 (s, br, 4H).

$^{13}$C NMR (125.79 MHz, $D_2O$): δ 172.17, 168.64, 157.78, 152.89, 150.25, 146.36, 142.80, 131.30,

3) Synthesis of a Preparation Intermediate Compound

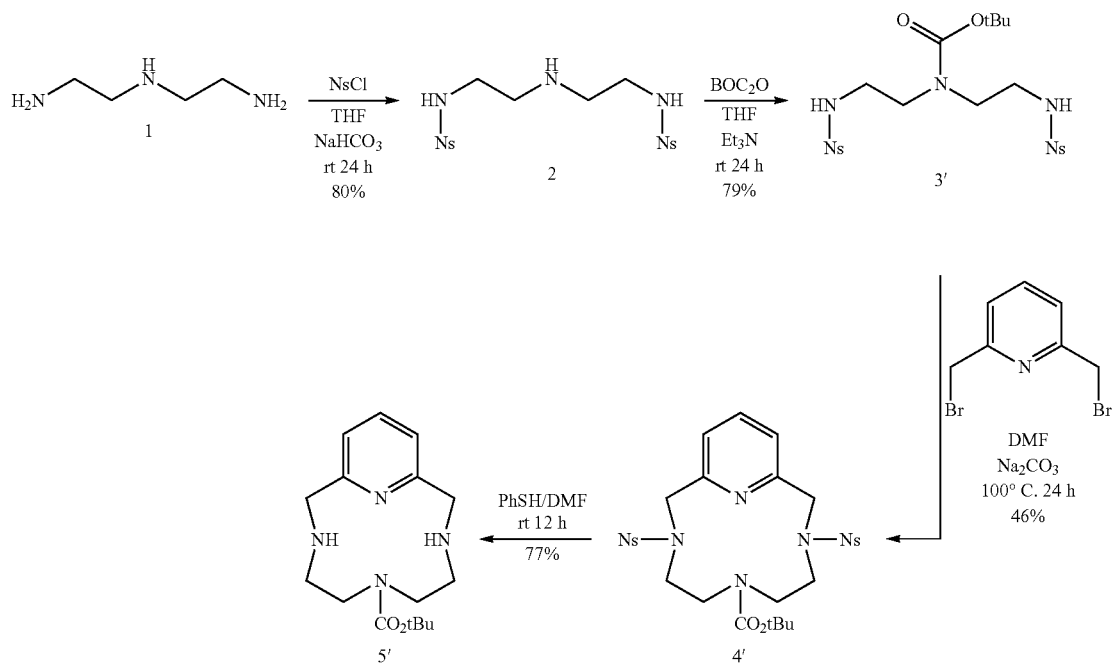

Synthetic scheme of example 3

Example 3—Int.3'

To a solution of compound 2 (Example 1-int.2) and of triethylamine (3.9 g, 38.8 mmol) in freshly distilled THF (150 ml) is added, at 0° C., a solution of di-tert-butyl dicarbonate (5.07 g, 23.3 mmol) in freshly distilled THF (50 ml). The medium is stirred at room temperature for 24 hours and then treated with saturated $NH_4Cl$ solution. The solvent is evaporated off under reduced pressure and the aqueous phase is washed with dichloromethane (3×80 ml). After drying over $MgSO_4$, the organic solution is filtered and concentrated under vacuum. The residue is chromatographed on silica gel (3/7 to 7/3 ethyl acetate/heptane) to give the expected compound in the form of a yellow oil (7.0 g, 79%).

$^1$H NMR (300 MHz, $CDCl_3$): δ 8.05-7.63 (m, 2H), 7.79-7.63 (m, 6H), 5.99 (s, br, 1H), 5.77 (s, br, 1H), 3.3 (m, 4H), 3.19 (m, 4H), 1.37 (s, 9H).

$^{13}$C NMR (75.47 MHz, $CDCl_3$): δ 155.78, 147.75, 133.77, 133.09, 132.95, 130.71, 125.20, 80.85, 42.34, 28.16.

Example 3—Int.4'

To a mixture composed of the product prepared previously (7.0 g, 12.2 mmol), $Na_2CO_3$ and DMF (200 ml) heated to 100° C. is added, under a nitrogen atmosphere, a solution of 2,6-bis(bromomethyl)pyridine (3.23 g, 12.2 mmol) in 100 ml of dry DMF. The medium is stirred at 100° C. for 24 hours and then cooled. The solvent is evaporated off under reduced pressure and the residue thus obtained is taken up in $CH_2Cl_2$. The organic phase is washed with 1M NaOH solution and dried with $MgSO_4$. After filtration and concentration, the product is precipitated from acetone to give a white solid (3.76 g, 46%).

$^1$H NMR (300 MHz, DMSO-$d_6$): δ 8.10-7.80 (m, 9H), 7.35 (m, 2H), 4.60 (s, 4H), 3.53 (s, 8H), 1.38 (s, 9H).

$^{13}$C NMR (75.47 MHz, DMSO-$d_6$): δ 155.83, 155.75, 154.59, 147.95, 147.89, 138.40, 135.63, 134.57, 132.75, 132.62, 131.17, 130.97, 129.52, 129.19, 124.62, 124.63, 122.49, 122.44, 78.81, 55.17, 50.02, 49.79, 45.42, 44.72, 44.66, 43.09, 27.97.

Example 3-Int.5'

To a suspension of $Na_2CO_3$ in 250 ml of DMF are added the compound prepared previously (3.59 g, 5.43 mmol) and then thiophenol (2.35 g, 21.3 mmol). The mixture is stirred at room temperature for 12 hours, the solvent is then evaporated off under reduced pressure and the residue obtained is taken up in $CH_2Cl_2$. The organic phase is washed with water, dried over $MgSO_4$ and then filtered and concentrated. The residue thus obtained is purified by chromatography on silica gel (100/0 to 95/5 MeOH/32% $NH_3$aq) to give the expected compound in the form of a yellow oil (1.06 g, 76%).

$^1$H NMR (300 MHz, $CDCl_3$): δ 7.51 (t, 1H, $^3$J=7.5 Hz), 6.94 (d, 2H, $^3$J=7.5 Hz), 3.94 (s, 4H), 3.52 (t, 4H, $^3$J=5.1 Hz), 3.04 (s, 2H), 2.61 (t, 4H, $^3$J=5.65 Hz), 1.49 (s, 9H).

$^{13}$C NMR (75.47 MHz, $CDCl_3$): δ 158.22, 157.53, 136.65, 120.34, 80.27, 52.06, 50.78, 48.88, 28.59.

4) Synthesis of the Ligand Pc2a1pa Sym P04218 of Formula (I) Via the "Boc" Route Synthetic scheme of example 4

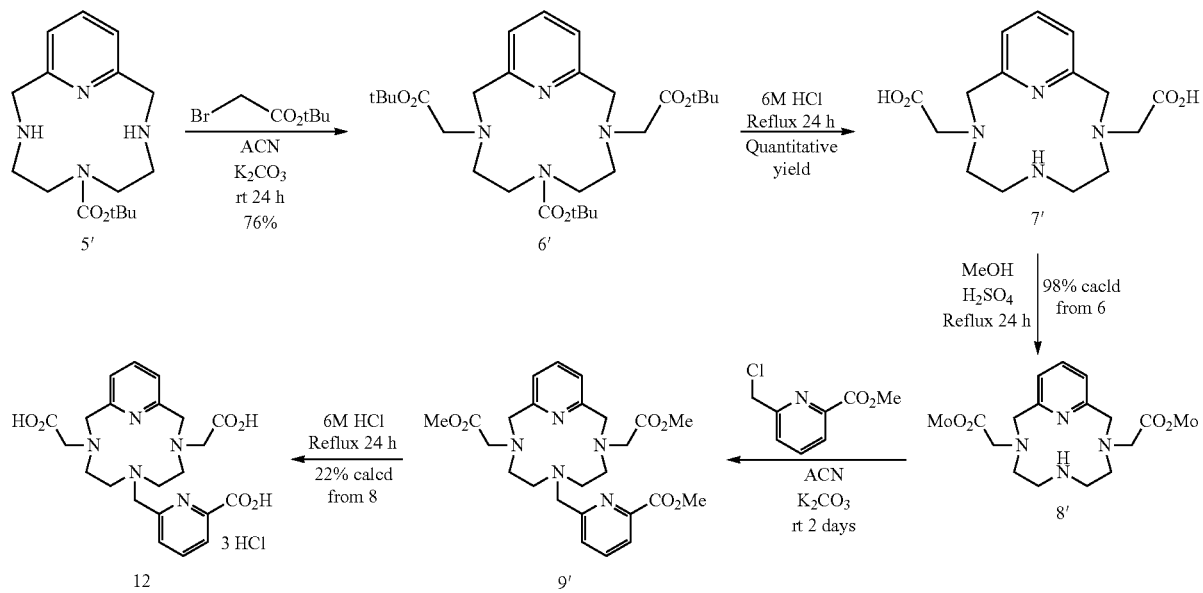

Example 4-Int.6'

To a mixture composed of the product obtained previously (Example 3-int.5') (0.803 g, 2.62 mmol) and $K_2CO_3$ in 150 ml of acetonitrile is added a solution of tert-butyl bromoacetate (1.022 g, 5.24 mmol) in 50 ml of acetonitrile and the mixture is stirred at room temperature for 24 hours. The solvent is evaporated off, the residue is taken up in $CH_2Cl_2$ and the solution obtained is then filtered and concentrated. The product is purified by chromatography on silica gel (100/0 to 98/2 $CH_2Cl_2$/MeOH) to give a yellow oil (1.06 g, 76%).

$^1$H NMR (300 MHz, CDCl$_3$): δ 7.5 (t, 1H, $^3$J=7.5 Hz), 7.08 (d, 2H, $^3$J=7.5 Hz), 3.86 (s, br, 4H), 3.27 (d, 4H, $^3$J=9.4 Hz), 3.01 (m, 4H), 2.75-2.55 (m, 4H), 1.34 (s, 18H), 1.24 (s, 9H).

$^{13}$C NMR (75.47 MHz, CDCl$_3$): δ 170.45, 170.27, 157.44, 156.97, 155.26, 137.18, 122.67, 122.61, 80.75, 78.71, 59.99, 59.60, 59.02, 58.67, 51.77, 51.27, 45.04, 44.81, 28.21, 28.03.

Example 4-Int.7'

The compound prepared previously (1.06 g, 9.5 mmol) is dissolved in 20 ml of 6M hydrochloric acid and the mixture is refluxed overnight. After cooling, the solvent is evaporated off and the expected product is obtained in the form of a brown solid (100%).

$^1$H NMR (300 MHz, D$_2$O): δ 7.91 (t, 1H, $^3$J=7.9 Hz), 7.36 (d, 2H, $^3$J=7.9 Hz), 4.20 (s, 4H), 3.65 (s, 4H), 2.96 (m, 4H), 2.78 (m, 4H).

$^{13}$C NMR (75.47 MHz, D$_2$O): δ 175.61, 154.59, 147.87, 127.29, 60.26, 59.52, 54.14, 46.69.

Example 4-Int.8'

To a solution of the compound obtained previously in 30 ml of methanol is added 5 ml of concentrated $H_2SO_4$ and the mixture is then stirred and refluxed overnight. After cooling, the solvent is evaporated off, the residue is taken up in 10 ml of water and the pH is adjusted to 7 by adding $K_2CO_3$. The water is evaporated off and the residue is taken up in dichloromethane. The organic phase is then dried over MgSO$_4$, filtered and concentrated. The expected product is obtained in the form of yellow oil (0.67 g, 98% calc. starting from 6').

$^1$H NMR (300 MHz, CDCl$_3$): δ 7.34 (t, 1H, $^3$J=7.5 Hz), 6.84 (d, 2H, $^3$J=7.5 Hz), 3.86 (s, 4H), 3.51 (s, 10H), 2.69 (m, 4H), 2.02 (m, 4H).

$^{13}$C NMR (75.47 MHz, CDCl$_3$): δ 172.12, 159.24, 136.56, 120.66, 59.54, 57.73, 52.59, 50.95, 46.99.

Example 4-Int.9'

To a mixture composed of the product obtained previously (0.67 mg, 1.9 mmol) and $K_2CO_3$ (0.524 g, 3.8 mmol) in 50 ml of acetonitrile is added 0.353 g (1.9 mmol) of the methyl ester of 6-chloromethyl-2-pyridinecarboxylic acid and the medium is stirred for two days at room temperature. The solvent is evaporated off and the residue is taken up in $CH_2Cl_2$ and then filtered. The solution obtained is concentrated and the product is used directly in the following step without further purification.

Example 4-Int.12

To the compound prepared previously are added 20 ml of 6M hydrochloric acid and the mixture is refluxed overnight. The solvent is evaporated off and the residue obtained is purified by HPLC on a C18 phase (100/0 to 10/90 H$_2$O 0.1% HCl/acetonitrile) to give the expected product in the form of a colorless oil (0.237 g, 22% calc. starting from 8' for 3 HCl).

$^1$H NMR (500.25 MHz, D$_2$O): δ 8.33 (t, 1H, $^3$J=7.8 Hz), 8.25 (d, 1H, $^3$J=7.8 Hz), 8.07 (d, 1H, $^3$J=7.8 Hz), 8.00 (t, 1H, $^3$J=7.8 Hz), 7.49 (d, 2H, $^3$J=7.8 Hz), 4.81 (s, 4H), 4.20 (s, 2H), 3.76 (s, 4H), 3.63 (m, 4H), 2.99 (s, br, 4H).

$^{13}$C NMR (125.79 MHz, D$_2$O): δ 172.17, 168.64, 157.78, 152.89, 150.25, 146.36, 142.80, 131.30, 128.33, 125.60, 62.35, 60.08, 59.47, 56.09, 52.88.

5) Synthesis of the Ligand Pc1a2pa Sym P04213 of Formula (I) Via the "Boc" Route Synthetic scheme of example 5

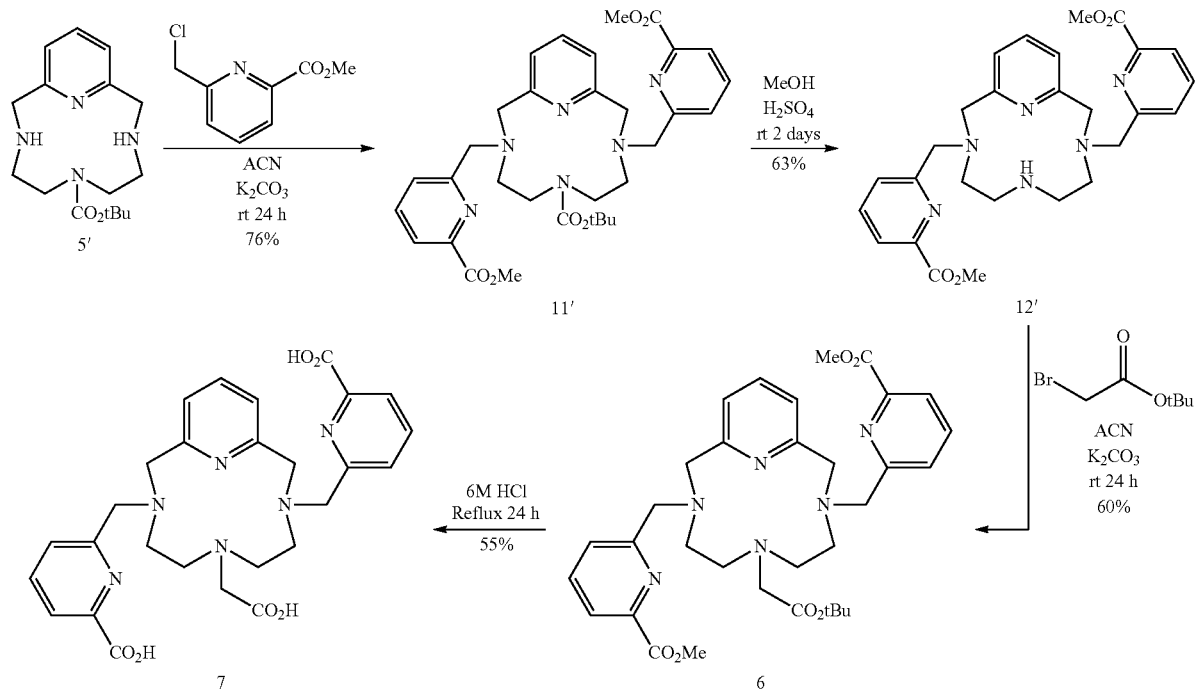

Example 5-Int.11'

To a mixture composed of the product obtained previously (Example 3-int.5') (0.326 g, 1.06 mmol) and $K_2CO_3$ (0.587 g, 4.3 mmol) in 50 ml of acetonitrile is added a solution of the methyl ester of 6-chloromethyl-2-pyridinecarboxylic acid (0.395 g, 2.13 mmol) in 20 ml of acetonitrile. The mixture is stirred at room temperature for 5 days and the solvent is evaporated off. The residue is taken up in dichloromethane and the suspension is filtered. The chloromethylene solution is concentrated and the residue is purified by chromatography on neutral alumina (100/0 to 98/2 $CH_2Cl_2$/MeOH) to give a yellow oil (0.407 g, 63%).

$^1$H NMR (300 MHz, $CDCl_3$): δ 8.05-7.95 (m, 2H), 7.87-7.73 (m, 4H), 7.66 (t, 1H, $^3J$=7.2 Hz), 7.2 (m, 2H), 4.10-3.80 (m, 14H), 3.46-3.31 (m, 4H), 2.75-2.50 (m, 4H), 1.17 (s, 9H).

$^{13}$C NMR (75.47 MHz, $CDCl_3$): δ 165.91, 160.82, 160.70, 156.80, 156.54, 155.48, 147.44, 137.66, 137.55, 137.38, 126.14, 126.07, 123.83, 23.14, 122.96, 79.03, 62.90, 62.71, 59.96, 58.78, 53.00, 51.59, 51.27, 45.14, 44.75, 28.30.

Example 5-Int.12'

To a solution of the compound prepared previously (0.407 g, 0.67 mmol) in 20 ml of methanol is added 1 ml of concentrated sulfuric acid. The mixture is stirred at reflux for 2 days. After cooling, the solvent is evaporated off, the residue is taken up in water (10 ml) and the pH of the medium is adjusted to 7 by adding $K_2CO_3$. The water is evaporated off and the residue is taken up in dichloromethane. The organic phase is dried over magnesium sulfate, filtered and concentrated. The product is purified by chromatography on neutral alumina (100/0 to 98/2 $CH_2Cl_2$/MeOH) to give a yellow oil (0.214 g, 63%).

$^{13}$C NMR (75.47 MHz, $CDCl_3$): δ 165.60, 159.30, 159.24, 146.64, 137.17, 127.10, 123.58, 119.79, 61.92, 57.51, 52.72, 52.56, 46.12.

Example 5-Int.6

To a mixture of the compound prepared previously (0.214 g, 0.423 mmol) and $K_2CO_3$ (0.117 g, 0.85 mmol) in 20 ml of acetonitrile is added a solution of tert-butyl bromoacetate (0.083 g, 0.423 mmol) in 10 ml of acetonitrile. The mixture is stirred at room temperature for 24 hours and then concentrated. The residue is taken up in $CH_2Cl_2$ and the salts are filtered off. After evaporating off the solvent, the residue is purified by chromatography on neutral alumina (100/0 to 98/2 $CH_2Cl_2$/MeOH) to give the expected product in the form of a yellow oil (0.155 g, 60%).

Example 5-Int.7

The compound obtained previously is dissolved in 20 ml of 6M hydrochloric acid and the mixture is refluxed overnight. After evaporating off the water, the residue is purified by HPLC on a $C_{18}$ phase (100/0 to 90/10 $H_2O$/ACN) to give a colorless oil (0.089 g, 55% calc. for 3 HCl).

$^1$H NMR (500.25 MHz, $D_2O$): δ 8.21 (t, 2H, $^3J$=7.8 Hz), 8.07 (d, 2H, $^3J$=7.8 Hz), 7.88 (d, 2H, $^3J$=7.8 Hz), 7.68 (t, 1H, $^3J$=7.8 Hz), 7.07 (d, 2H, $^3J$=7.8 Hz), 4.63 (s, 4H), 4.45 (s, br, 4H), 3.78 (s, 2H), 3.58 (m, 4H), 3.46 (s, br, 4H).

$^{13}$C NMR (125.79 MHz, $D_2O$): δ 175.11, 170.44, 157.33, 153.78, 152.13, 145.76, 142.12, 131.02, 127.79, 124.63, 62.55, 60.72, 57.63, 56.20, 54.67.

REFERENCES

1. Schwarzenbach, G.; Flaschka, W. *Complexometric Titrations*; Methuen & Co.: London, 1969.
2. Gans, P.; Sabatini, A.; Vacca, A. *Talanta* 1996, 43, 1739-1753.
3. Alderighi, L.; Gans, P.; Ienco, A.; Peters, D.; Sabatini, A.; Vacca, A. *Coord. Chem. Rev.* 1999, 184, 311-318.

6) Synthesis of the Ligand Pc1a2pa Asym P04214 of Formula (I) Via the "Oxalate" Route

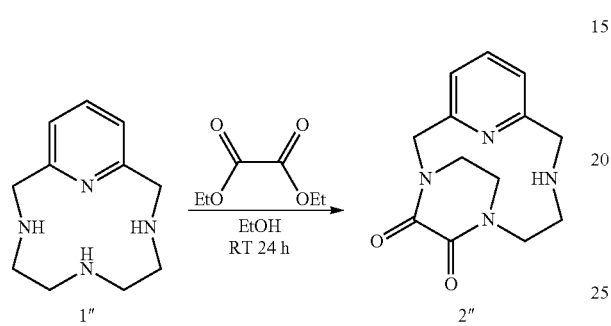

solution of diethyl oxalate (2.02 g, 13.8 mmol) in EtOH (100 mL) was added to a solution of pyclene (2.37 g, 11.5 mmol) in EtOH (200 mL). The mixture was stirred at room temperature overnight and then concentrated. The residue obtained was purified by chromatography on a column of alumina (98/2 $CH_2Cl_2$/MeOH). The final product was obtained in the form of a white solid (0.548 g, 19%).

$^1$H NMR (300 MHz, $CDCl_3$): δ 7.52 (t, 1H, $^3J$=7.7 Hz), 7.02 (d, 1H, $^3J$=7.9 Hz), 6.93 (d, 1H, $^3J$=7.5 Hz), 5.59 (d, 1H, $^2J$=16.2 Hz), 4.62 (ddd, 1H, $^2J$=13.9 Hz, $^3J$=11.1 Hz, $^3J$=2.5 Hz), 4.08 (d, 1H, $^2J$=16.6 Hz), 3.95 (d, 1H, $^2J$=17.3 Hz), 3.77 (ddd, 1H, $^2J$=13.9 Hz, $^3J$=10.6 Hz, $^3J$=4.52 Hz), 3.70 (d, 1H, $^2J$=17.3 Hz), 3.5 (ddd, 1H, $^2J$=12.4 Hz, $^3J$=10.6 Hz, $^3J$=4.5 Hz), 3.24 (dt, 1H, $^2J$=13.9 Hz, $^3J$=4.4 Hz), 3.13 (dt, 1H, $^2J$=12.4 Hz, $^3J$=4.1 Hz), 3.01 (dt, 1H, $^2J$=12.2 Hz, $^3J$=3.2 Hz), 2.83 (dt, 1H, $^2J$=13.9 Hz, $^3J$=3.0 Hz), 2.74 (td, 1H, $^2J$=11.7 Hz, $^3J$=2.3 Hz).

$^{13}$C NMR (75.47 MHz, $CDCl_3$): δ 162.96, 161.23, 159.10, 153.42, 136.83, 120.58, 119.44, 55.40, 52.53, 47.89, 47.66, 44.61, 44.20

Synthesis of the Pyclene Oxalate Intermediate 2":

Various tests were performed to obtain the "pyclene oxalate" intermediate 2", as indicated below.

Route 1

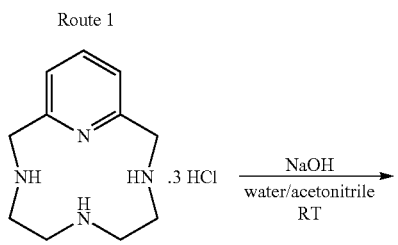

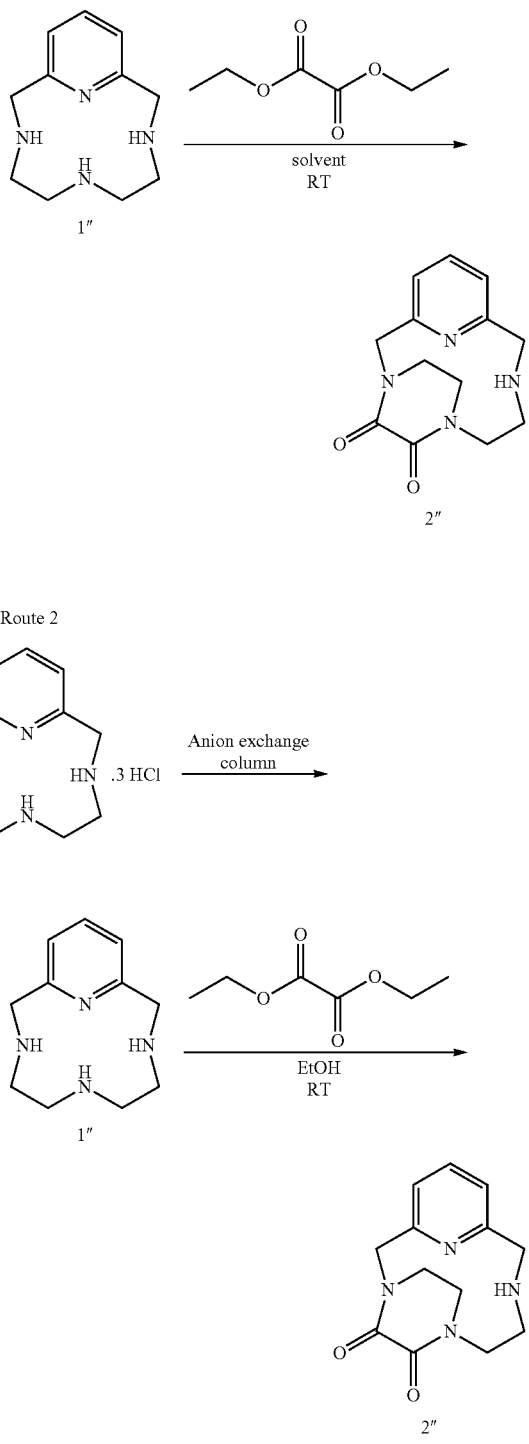

Route 2

Route 3

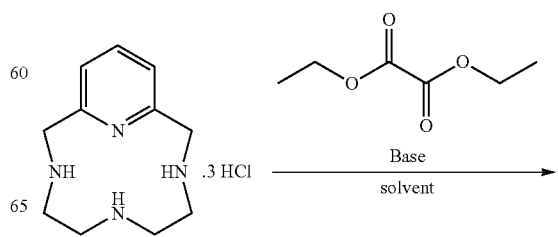

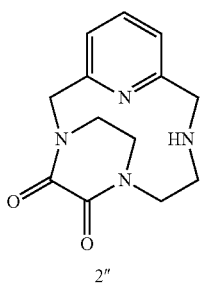 [SMILES: O=C1C(=O)N2CCN1CCNCc1cccc(n1)C2]

2″

| Test | Route used | Conditions | Purification | Yield |
|------|------------|------------|--------------|-------|
| 1 | 3 | DIPEA, EtOH, 2 days, RT | Precipitation | 22% |
| 2 | 1 | EtOH, 1.5 days, RT | Chromatography on alumina | 33% |
| 3 | 1 | EtOH, 2 days, RT | Chromatography on alumina | 36% |
| 4 | 2 | EtOH, 41 h, RT | Chromatography on alumina | 37% |
| 5 | 1 | MeOH, 48 h, RT | Precipitation | 54% |
| 6 | 1 | MeOH, 23 h, RT | Precipitation | 93% |

Summary of the tests on the synthesis of the pyclene oxalate intermediate 2″

It is observed that the "pyclene oxalate" intermediate 2″ is obtained according to the various operating conditions and routes tested. In particular, a very good yield is observed, greater than 90%, in the presence of methanol.

Continuation of the Synthesis:

concentrated. The desired product was obtained in the form of a yellow oil and used in the following steps without further purification (1.25 g).

$^1$H NMR (300 MHz, CDCl$_3$): δ 7.28 (t, 1H, $^3$J=7.7 Hz), 6.8 (d, 1H, $^3$J=7.5 Hz), 6.63 (d, 1H, $^3$J=7.5 Hz), 5.26 (d, 1H, $^2$J=16.6 Hz), 4.08 (m, 1H), 3.89 (d, 1H, $^2$J=16.6 Hz), 3.68 (m, 4H), 3.0 (m, 4H), 2.77 (m, 2H), 2.52 (m, 1H), 1.18 (m, 9H).

$^{13}$C NMR (75.47 MHz, CDCl$_3$): δ 170.65, 162.42, 159.73, 158.43, 153.60, 136.48, 119.67, 119.11, 80.37, 61.08, 56.45, 52.59, 52.07, 46.64, 46.07, 44.76, 27.61.

Compound 3″ was dissolved in MeOH (100 mL) and concentrated sulfuric acid (10 mL) was added slowly. The mixture was refluxed for 24 hours. After cooling to room temperature, the solvent was evaporated off. 20 mL of water were added and the pH was adjusted to 7 with K$_2$CO$_3$. The water was evaporated off and the residue was taken up in dichloromethane. Magnesium sulfate was added and the organic phase was filtered and then concentrated. The crude product was purified by chromatography on a column of alumina (98/2 to 95/5 CH$_2$Cl$_2$/MeOH). Compound 4″ is in the form of a white solid (0.939 g, 99% calculated starting from 2″).

$^1$H NMR (300 MHz, CDCl$_3$): δ 7.52 (t, 1H, $^3$J=7.5 Hz), 6.96 (m, 2H), 3.96 (d, 4H, $^3$J=9.8 Hz), 3.63 (m, 5H), 3.28 (m, 2H), 3.18 (m, 2H), 2.86 (dt, 4H, $^2$J=11.3, $^3$J=5.7 Hz).

$^{13}$C NMR (75.47 MHz, CDCl$_3$): δ 172.17, 161.02, 159.09, 137.57, 120.07, 119.97, 57.69, 57.04, 52.35, 51.72, 51.54, 46.80, 46.29, 46.23.

The methyl ester of chloromethyl-2-pyridinecarboxylic acid was added to a solution of compound 4″ (0.939 g, 3.38

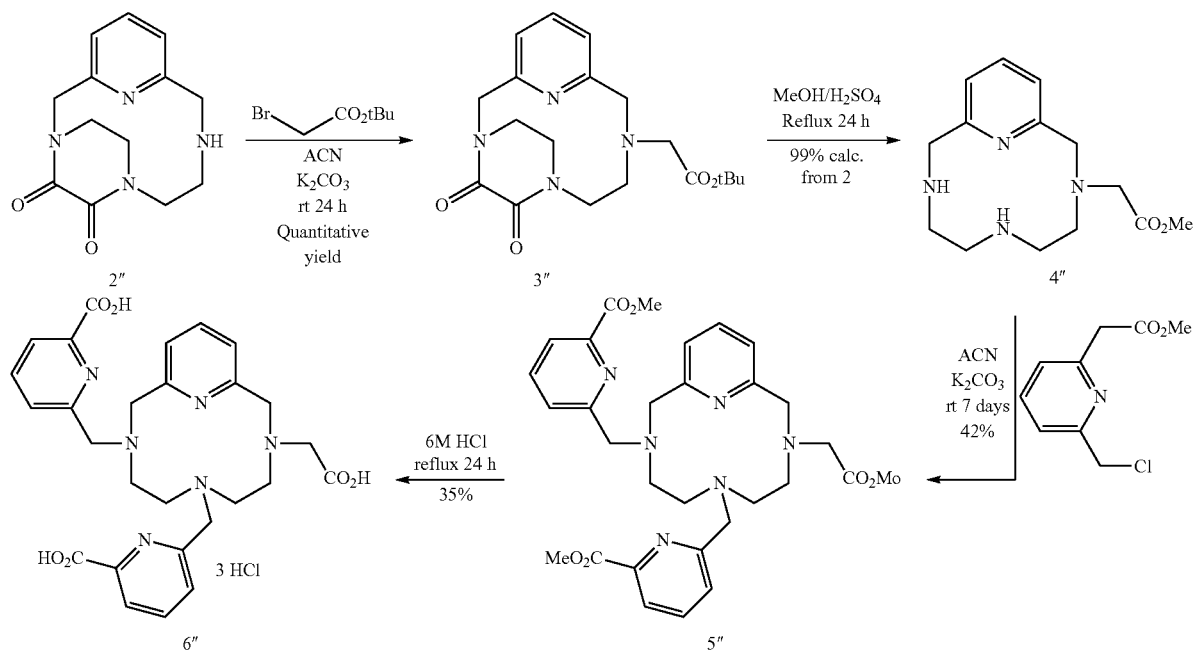

A solution of tert-butyl bromoacetate (0.668 g, 3.42 mmol) in acetonitrile (100 mL) was added to a solution of 2″ (0.890 g, 3.42 mmol) and K$_2$CO$_3$ (1.42 g, 10.3 mmol) in acetonitrile (150 mL). The mixture was stirred at room temperature for 24 hours. The solvent was evaporated off and the residue was taken up in dichloromethane and then filtered and mmol) in acetonitrile (150 mL) in the presence of K$_2$CO$_3$ (1.8 g, 13.5 mmol). The mixture was stirred at room temperature for one week and then filtered and concentrated. The crude product was purified by chromatography on a column of alumina (98/2 CH$_2$Cl$_2$/MeOH) to give compound 5″ in the form of a yellow oil (0.822 g, 42%).

Hydrochloric acid (20 mL, 6M) was added slowly to compound 5". The mixture was refluxed for 24 hours and then concentrated. The crude product was purified using C18 HPLC (90/10 to 5/95 H$_2$O 0.1% HCl/acetonitrile) and the ligand 6" was obtained in the form of a colorless oil (0.310 g, 35% calculated for 3 HCl).

$^1$H NMR (500 MHz, D$_2$O): δ 7.98-7.87 (m, 5H), 7.65 (d, 1H, $^3$J=7.3 Hz), 7.47 (m, 1H), 7.43 (d, 1H, $^3$J=7.9 Hz), 7.31 (d, 1H, $^3$J=7.9 Hz), 4.78 (s, 2H), 4.74 (s, br, 2H), 4.54 (s, 2H), 4.20 (s, 2H), 3.78 (s, br, 2H), 3.63 (s, br, 2H), 3.55 (s, 2H), 3.12 (m, 4H).

$^{13}$C NMR (125.77 MHz, D$_2$O): 172.25, 171.82, 170.66, 158.41, 153.72, 153.30, 152.78, 152.14, 151.95, 143.56, 142.61, 142.36, 130.33, 129.50, 127.63, 127.24, 125.33, 125.16, 61.91, 61.78, 61.72, 60.08, 56.17, 56.12, 53.57, 53.37

7) Synthesis of the Ligand Pc2a1pa Asym P04216 of Formula (I) Via the "Oxalate" Route The crude product was purified by chromatography on a column of alumina (98/2 to 95/5 CH$_2$Cl$_2$/MeOH) to give 8" in the form of a yellow oil (1.24 g, 92%).

A solution of tert-butyl bromoacetate (1.36 g, 6.98 mmol) in acetonitrile (150 mL) was added to a solution of 8" (1.24 g, 3.49 mmol) and K$_2$CO$_3$ (1.93 g, 14 mmol) in acetonitrile (150 mL). The mixture was refluxed for 2 days. The solvent was evaporated off and the residue was taken up in dichloromethane, filtered and concentrated. Compound 9" was obtained in the form of a yellow oil and used in the following step without further purification.

Hydrochloric acid (20 mL, 6M) was added slowly to compound 9". The mixture was refluxed for 24 hours and then concentrated. The crude product was purified using C18 HPLC (90/10 to 5/95 H$_2$O 0.1% HCl/acetonitrile) and the ligand 10" was obtained in the form of a colorless oil.

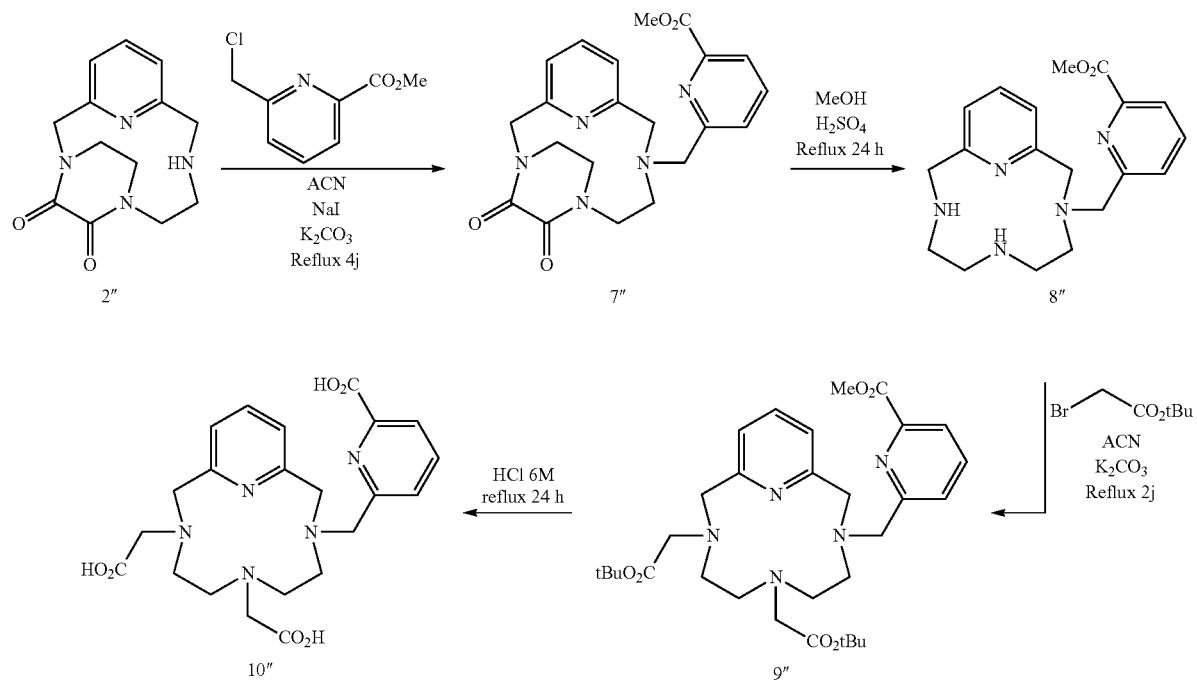

The methyl ester of 6-chloromethyl-2-pyridinecarboxylic acid (711 g, 3.85 mmol) was added to a solution of compound 2" (1.0 g, 3.85 mmol) in acetonitrile (300 mL) in the presence of K$_2$CO$_3$ (1.5 g, 12 mmol). The mixture was refluxed for 4 days and then filtered and concentrated. The crude product was purified by chromatography on a column of alumina (98/2 CH$_2$Cl$_2$/MeOH) to give compound 7" in the form of a yellow oil (1.56 g, 99%).

Compound 7" (1.56 g, 3.81 mmol) was dissolved in MeOH (40 mL) and concentrated sulfuric acid (1 mL) was added slowly. The mixture was refluxed for 24 hours. After cooling to room temperature, the solvent was evaporated off. 20 mL of water were added and the pH was adjusted to 7 with K$_2$CO$_3$. The water was evaporated off and the residue was taken up in dichloromethane. Magnesium sulfate was added and the organic phase was filtered and then concentrated.

8) Synthesis of the Ligand Pc3pa P04221 of Formula (I):

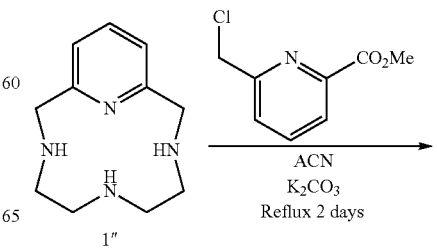

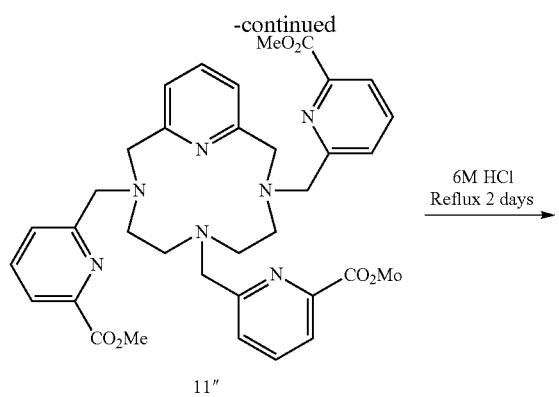

11″

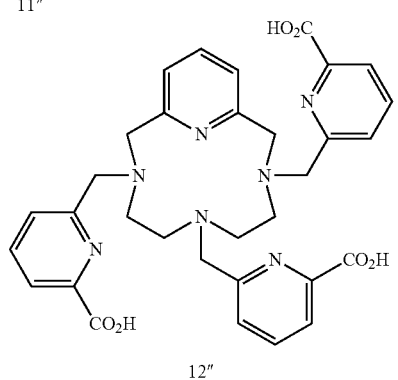

12″

The methyl ester of chloromethyl-2-pyridinecarboxylic acid (1.35 g, 7.28 mmol) was added to a solution of compound 1″ (0.50 g, 2.43 mmol) in acetonitrile (350 mL) in the presence of $K_2CO_3$ (1 g, 7.28 mmol). The mixture was refluxed for two days and then filtered and concentrated. The crude product was purified by chromatography on a column of alumina (98/2 $CH_2Cl_2$/MeOH). Compound 11″ is obtained in the form of a yellow oil (862 mg, 54%).

Hydrochloric acid (20 mL, 6M) was added to compound 11″ (862 mg, 1.32 mmol). The mixture was refluxed for 48 hours and then concentrated. The crude product was purified by precipitation from acetone. Compound 12″ was obtained in hydrochloride salt form (0.574 g, 57% calculated for 4 HCl).

$^1$H NMR (300 MHz, $D_2O$): δ 7.5-7.25 (m, 8H), 7.12-7.09 (m, 2H), 6.75 (d, 2H), 4.17 (s, 4H), 4.09 (s, 4H), 3.86 (s, 2H), 3.29 (m, 4H), 2.83 (m, 4H).

$^{13}$C NMR (75.47 MHz, $D_2O$): δ 170.11, 168.95, 158.31, 154.51, 153.79, 150.12, 149.48, 145.95, 144.50, 143.67, 132.57, 132.24, 129.55, 126.76, 62.60, 62.03, 60.78, 57.15, 54.14.

9-1) Synthesis of a Picolinate Bromide Derivative of Formula (II)

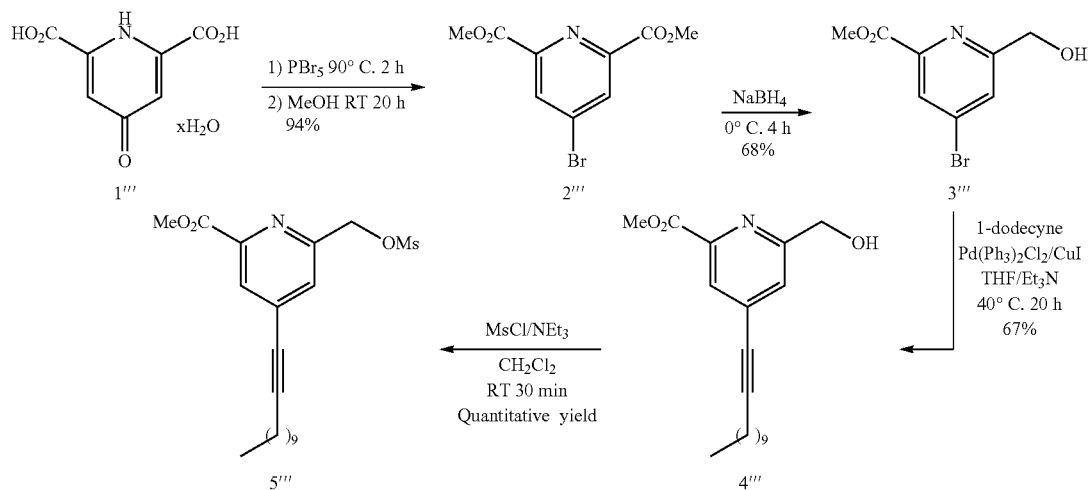

Chelidamic acid monohydrate 1‴ (5 g, 24.9 mmol) and phosphorus pentabromide (34 g, 79.0 mmol) were heated at 90° C. Once a liquid mixture was obtained, heating was continued for 2 hours at 90° C. After cooling the mixture with ice, chloroform (100 mL) and MeOH (100 mL) were added. The solution is mixed for 20 hours at room temperature and the pH is adjusted to 7 with saturated $NaHCO_3$ solution. The solvents were evaporated off and the aqueous phase was extracted using dichloromethane (3×100 mL). The organic phase was dried over $MgSO_4$, filtered and concentrated to give compound 2‴ in the form of a white solid (6.43 g, 94%).

$^1$H NMR (300 MHz, $CDCl_3$): δ 8.42 (s, 2H), 3.99 (s, 6H).

$^{13}$C NMR (300 MHz, $CDCl_3$): δ 164.02, 149.12, 135.13, 131.33, 53.52.

Compound 2‴ (6.43 g, 23.5 mmol) was dissolved in dichloromethane (50 mL) and methanol (70 mL). $NaBH_4$ (1.02 g, 28.2 mmol) was added portionwise to the mixture at 0° C., under nitrogen. After stirring for 4 hours, hydrochloric acid was added to adjust the pH to 5. The solvents were evaporated off and the pH of the aqueous phase was adjusted to 12 with $Na_2CO_3$. The aqueous phase was extracted with dichloromethane (3×100 mL) and the organic phase was dried with $MgSO_4$, filtered and concentrated under vacuum. After purification on alumina, compound 3‴ was obtained in the form of a white solid (3.92 g, 68%).

$^1$H NMR (300 MHz, CDCl$_3$): δ 8.12 (s, 1H), 7.76 (s, 1H), 4.82 (s, 2H), 3.95 (s, 3H).

$^{13}$C NMR (300 MHz, CDCl$_3$): δ 164.55, 162.33, 147.96, 134.66, 127.31, 127.21, 64.49, 53.29.

Under an inert atmosphere, Pd(Ph$_3$)$_2$Cl$_2$ (232 mg, 0.33 mmol) and CuI (124.2, 0.65 mmol) were added to a degassed solution of 1-dodecyne (651 mg, 3.92 mmol) in triethylamine (10 mL) and 3''' (800 mg, 3.26 mmol) in freshly distilled THF. The mixture was stirred at 40° C. for 20 hours. After cooling to room temperature, the suspension was filtered and triturated with Et$_2$O (40 mL). The filtrate was washed with saturated NH$_4$Cl solution (2×50 mL) and brine (40 mL). Finally, the organic phase was dried over MgSO$_4$, filtered and concentrated under vacuum. The crude product was purified on silica gel (7/3 to 4/6 hexane/ethyl acetate) to give compound 4''' in the form of a white solid (727 mg, 67%).

$^1$H NMR (300 MHz, CDCl$_3$): δ 7.93 (s, 1H), 7.48 (s, 1H), 4.80 (s, 2H), 3.95 (s, 3H), 2.41 (t, 2H), 1.58 (m, 2H), 1.5-1.1 (m, 14H), 0.85 (t, 3H).

$^{13}$C NMR (300 MHz, CDCl$_3$): δ 165.37, 160.62, 147.05, 134.54, 126.15, 125.98, 97.83, 78.05, 64.62, 53.02, 31.99, 29.67, 29.59, 29.40, 29.21, 29.01, 28.39, 22.77, 19.60, 14.20.

Compound 4''' (727 mg, 2.15 mmol) was dissolved in dichloromethane (80 mL) and triethylamine (653 mg, 6.45 mmol). Mesyl chloride (369 mg, 3.23 mmol) was added and the mixture was stirred at room temperature for 30 minutes. The organic phase was washed with saturated aqueous sodium hydrogen carbonate solution (100 mL) and then dried over MgSO$_4$, filtered and concentrated. Compound 5''' is obtained in the form of a white solid (896 mg, quantitative yield).

9-2) Synthesis of the Ligand Pc1a2pa Asym C12 P04245 of Formula (I):

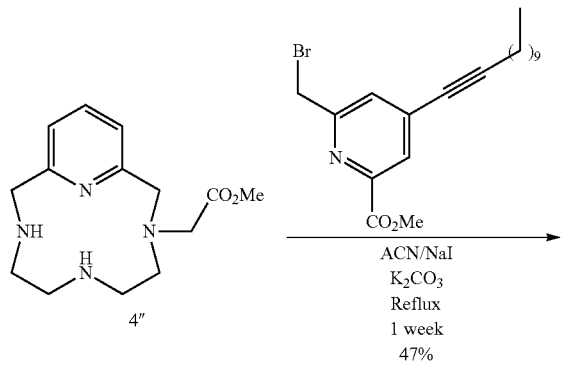

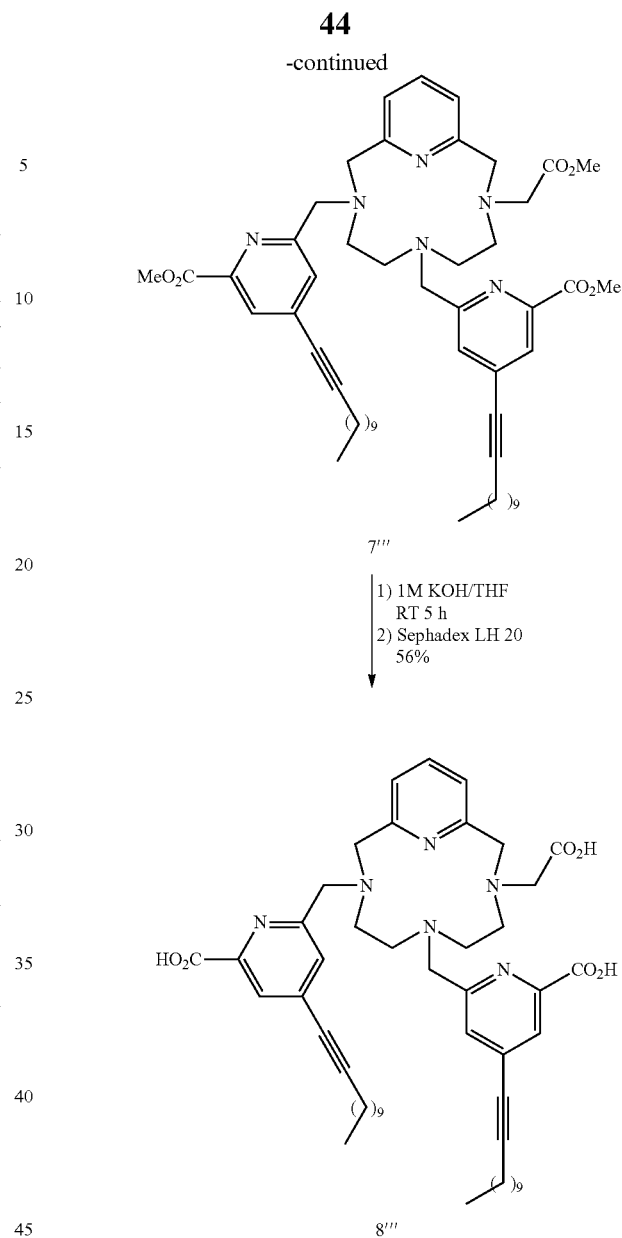

A solution of compound 5''' (712 mg, 1.75 mmol) in acetonitrile (50 mL) was added to a solution of compound 4'' (243 mg, 0.87 mmol) in refluxing acetonitrile (100 mL) in the presence of K$_2$CO$_3$ (361 g, 2.6 mmol). The mixture was refluxed for one week. After cooling to room temperature, the suspension was filtered and the solvent was evaporated off. The crude product was purified by chromatography on a column of alumina to give compound 7''' in the form of a yellow oil.

Production and Purification of the Ligand Pc1a2pa Asym C12 P04245: Saponification Step A solution of KOH (5 mL, 1M) was added to a solution of compound 7''' (91 mg, 0.10 mmol) in THF (6 mL). The mixture was stirred vigorously for 5 hours at room temperature. The organic phase was evaporated and the residue was then purified by exclusion chromatography (Sephadex LH20, 100/0 to 90/10 CH$_2$Cl$_2$/MeOH). Product 8''' was obtained in the form of a colorless solid (48 mg, 56%).

10) Synthesis of the Analog Pc1a2pa Asym C8 P04330:
10-1) Synthesis of a C8 Picolinate Bromide Derivative

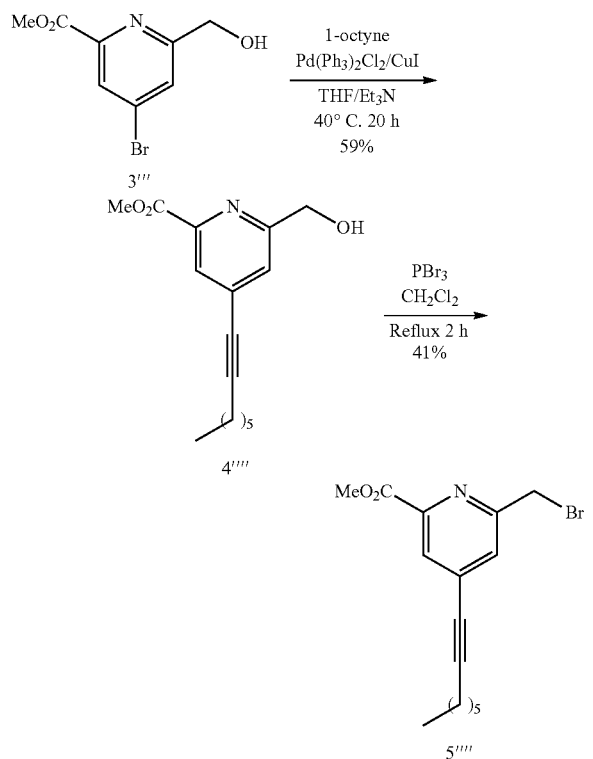

Under an inert atmosphere, Pd(Ph$_3$)$_2$Cl$_2$ (246 mg, 0.35 mmol) and CuI (134, 0.70 mmol) were added to a degassed solution of 1-octyne (464 mg, 4.21 mmol) in triethylamine (10 mL) and 3''' (863 mg, 3.51 mmol) in freshly distilled THF (20 mL). The mixture was stirred at 40° C. for 20 hours. After cooling to room temperature, the suspension was filtered and triturated with Et$_2$O (40 mL). The filtrate was washed with saturated NH$_4$Cl solution (2×20 mL) and brine (20 mL). Finally, the organic phase was dried over MgSO$_4$, filtered and concentrated under vacuum. The crude product was purified on silica gel (7/3 to 4/6 hexane/ethyl acetate) to give compound 4'''' in the form of a white solid (573 mg, 59%).

$^1$H NMR (300 MHz, CDCl$_3$): δ 7.69 (s, 1H), 7.39 (s, 1H), 4.63 (s, 2H), 3.74 (s, 3H), 2.22 (t, 2H), 1.40 (m, 2H), 1.24 (m, 2H), 1.35-1.15 (m, 4H), 0.69 (t, 3H).

$^{13}$C NMR (300 MHz, CDCl$_3$): δ 164.88, 161.27, 146.43, 133.96, 125.53, 125.35, 97.05, 77.74, 64.26, 52.45, 30.96, 28.25, 27.94, 22.18, 19.12, 13.66.

A solution of compound 4'''' (573 mg, 2.08 mmol) in anhydrous CH$_2$Cl$_2$ (50 mL) was cooled to 0° C. under an inert atmosphere. PBr$_3$ (676 mg, 2.5 mmol) was added and the mixture was then refluxed for 2 hours. After cooling to room temperature, the reaction medium was neutralized with 50 mL of water and K$_2$CO$_3$ to pH 7. The organic phase was dried over MgSO$_4$, filtered and then concentrated under vacuum. After purification on silica gel (9/1 to 4/6 hexane/ethyl acetate), product 5''' was obtained in the form of a white solid (289 mg, 41%).

$^1$H NMR (300 MHz, CDCl$_3$): δ 7.91 (s, 1H), 7.54 (s, 1H), 4.52 (s, 2H), 3.93 (s, 3H), 2.37 (t, 2H), 1.54 (m, 2H), 1.37 (m, 2H), 1.3-1.2 (m, 4H), 0.85 (t, 3H).

$^{13}$C NMR (300 MHz, CDCl$_3$): δ 165.00, 157.39, 147.63, 134.85, 128.82, 126.58, 98.23, 77.60, 53.04, 32.80, 31.25, 28.55, 28.18, 22.48, 19.48, 14.01.

10-2) Synthesis of the Ligand Pc1a2pa Asym C8 P04330

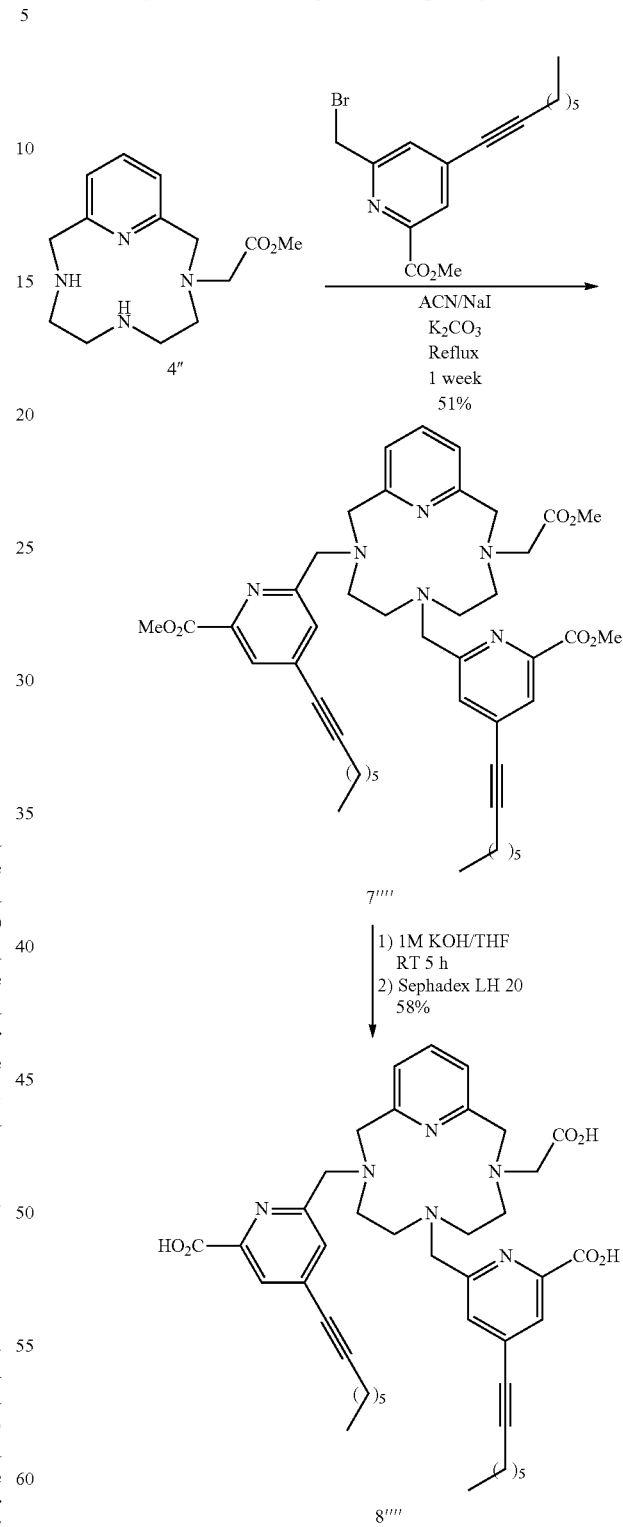

Compound 5'''' (289 mg, 0.85 mmol) was added to a solution of compound 4'' (106 mg, 0.38 mmol) in anhydrous acetonitrile (30 mL) in the presence of K$_2$CO$_3$ (158 mg, 1.1 mmol). The mixture was refluxed for one week. After cooling to room temperature, the suspension was filtered and the solvent was evaporated off. The crude product was dissolved in a minimum amount of ethyl acetate and pentane was then added until the solution became cloudy. The oil formed was rinsed with pentane and precipitated again. Compound 7"" was obtained in the form of a yellow oil (155 mg, 51%).

A solution of KOH (2 mL, 1M) was added to a solution of compound 7"" (55 mg, 0.069 mmol) in THF (5 mL). The mixture was stirred vigorously for 5 hours at room temperature. The organic phase was evaporated and the residue was then purified by exclusion chromatography (Sephadex LH20, 100/0 to 90/10 $CH_2Cl_2$/MeOH). Product 8"" was obtained in the form of a colorless solid (30 mg, 58%).

C— Study of the Compounds of Formula (I) and of the Complexes According to the Invention C-1 Synthesis of the Yttrium Complexes 1) The procedure for synthesizing the complex Y-Pc1a2pa sym P04183 is described below and is applicable to all of the ligands of general formula (I):

The ligand P04213 is dissolved in ultra-pure water and the pH is adjusted to 5 with 1M sodium hydroxide solution. The salt $YCl_3 \cdot 6H_2O$ (1.5 eq) is dissolved in ultra-pure water. The yttrium solution is added to the ligand solution with stirring. After adjusting the pH to 5, the solution is refluxed overnight. The complex is then purified by HPLC on C18 (100/0 to 10/90 $H_2O$/ACN) according to the scheme below:

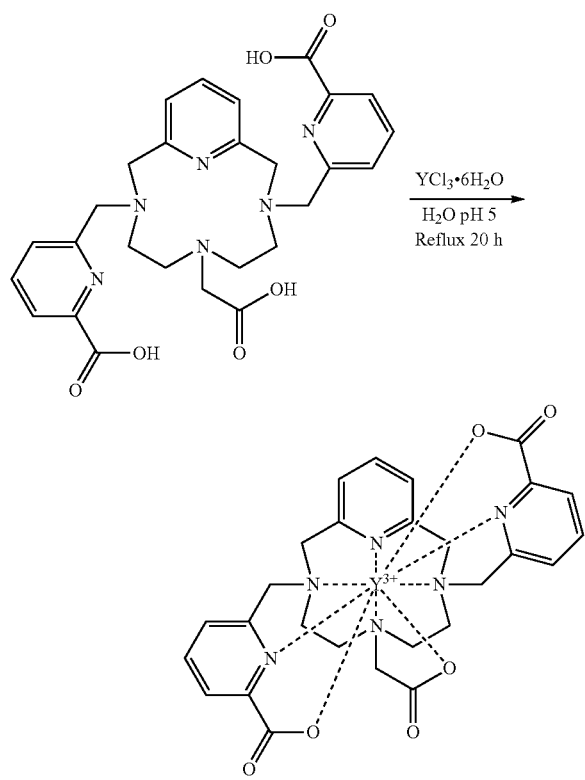

2) Synthesis of an yttrium-90 complex, P04233:

The ligand P04214 was used in a complexation reaction with yttrium-90 in order to confirm the complexation results obtained with non-radioactive natural yttrium. A radiolabeling study was performed.

The parameters studied are as follows:

| Parameters | Study range | Optimum |
| --- | --- | --- |
| pH | 1-9 | 6.5-9 |
| Temperature | 20-100° c. | 80° c. |
| Ligand concentration Mol/L | $10^{-5}$-$10^{-2}$ mol/L | $10^{-4}$-$10^{-2}$ mol/L |
| Time Min. | 5-60 min. | 15 min |

In summary, the optimum conditions for labeling P04214 are yttrium-90 in acetate medium pH=6.5-9, the ligand P04214 between $10^{-4}$ and $10^{-2}$ M in EtOH; 15 min at 80° C. The radiolabeling yield obtained is >90% (P04233).

3) Procedure for and result of labeling of the ligand P04245 with yttrium-90, production of the complex P04283:

The parameters studied are as follows:

| Parameters | Study range | Optimum |
| --- | --- | --- |
| pH | 4.65-9 | 6.5-9 |
| Temperature | 20-90° c. | 50° c. |
| Ligand concentration Mol/L | $10^{-5}$-$10^{-3}$ mol/L | $10^{-3}$ mol/L |
| Time Min. | 5-60 min. | 15 min |

The optimum labeling conditions are:
 yttrium-90 in acetate medium;
 pH=4.65-9;
 ligand P04245 at $10^{-3}$ M in EtOH;
 for 15 min at 50° C.

4) Procedure for and result of extraction of the complex P04283 with Lipiodol, production of P04284:

The solution containing the complex P04283 was made up to 2 mL with 1 mL of saline, and an equivalent volume of Lipiodol (2 mL) was added to the solution containing the complex. After stirring and centrifugation, the phases are separated and counted. The yield for extraction into Lipiodol is 89.8±5.0% (n=3).

5) Procedure for and results of the stability tests in human physiological saline:

Procedure for Preparing the Radiotracer P04284

1 mL of yttrium-90 acetate at pH=7 is added to 1 mL of ligand P04245 dissolved in ethanol at a concentration of $10^{-3}$ mol/L to form the complex P04283. The solution is heated for 30 minutes at 90° C. 2 mL of Lipiodol are added and the mixture is stirred vigorously. The phases are separated by centrifugation (3500 rpm, 15 minutes). The lipiodol-based phase is collected and made up to 2 mL with Lipiodol to give the expected radiotracer P04284.

1 mL of freshly prepared radiotracer is taken and then deposited in a 12 mL flat-bottomed glass flask. The activity is measured with an activimeter, and the time is noted. 10 mL of 0.9% saline solution (physiological saline) are added and the mixture is stirred. The flask is then placed in the incubator set at 37° C., equipped with a stirrer set at 30 rpm (revolutions per minute).

The system is left stirring for several days. The aqueous phase is sampled at various times to assay the yttrium-90 released. Each sample was taken in triplicate.

Figure 5:
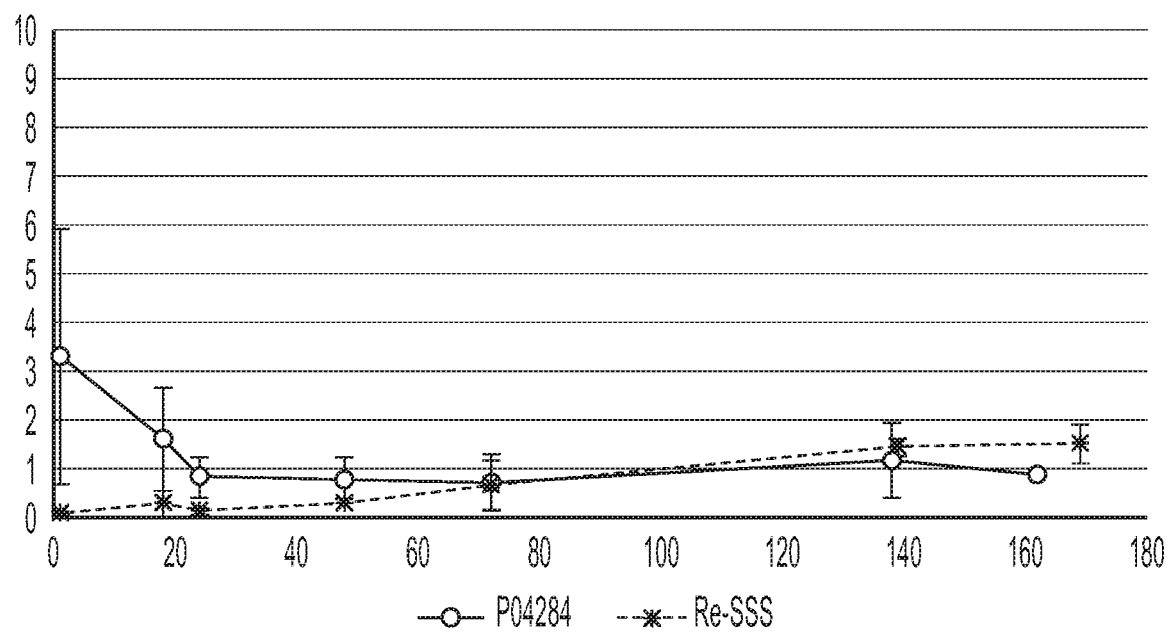
FIG. 5: Percentage of extraction of the complex P04283 with $^{90}$Y as a function of time, in hours (Re-SSS is a reference complex).

The results are given in FIG. 5. The complexes formed according to the invention and vectorized with Lipiodol are stable in physiological saline.

C-2 Synthesis of the Lanthanide Complexes:

1) The complexation reactions of gadolinium with the ligands P04218 and P04216 and also with ligand P04213 are performed in water in the presence of one equivalent of $GdCl_3$ at pH 5-6 at reflux overnight.

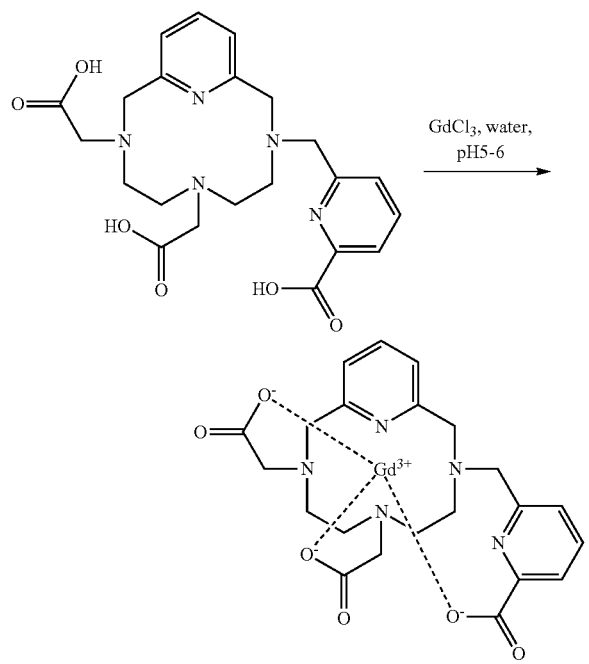

Example: Complexation of the Ligand P04216 with Gadolinium

Purification of the complexes is performed by preparative HPLC so as to remove the remaining salts.

2) Study of the Relaxivity of the Gadolinium Complexes:

The relaxivity studies were performed on the gadolinium complexes of the ligands P04218, P04216 and P04213, on Minispec Mq-20 and Minispec Mq-60 machines (Brüker, Karlsruhe, Germany) at 20 MHz (0.47 T) and 60 MHz (1.4 T) in water at 37° C.

For each complex prepared previously, a [Gd]concentration range extending from 0.5 to 5 mM was prepared and the values T1 and T2 of each of these solutions were then measured to determine the relaxivity values r1 and r2 by means of equation 1. For each of the ligands, a trend curve whose correlation coefficient was equal to or very close to 1 was obtained, which made it possible to check equation 1 and to validate the quality of the measurements taken. The curves plotted make it possible to determine the relaxivity value "r" which corresponds to coefficient "a" of the equation for the straight line "ax+b".

$$r = \frac{1}{[Gd^{3+}]}\left(\frac{1}{T_{obs}} - \frac{1}{T_{H2O}}\right)$$

Equation 1: General Formula for Calculating the Relaxivity Values r1 and r2

| Relaxivity (mmol$^{-1}$s$^{-1}$) | 20 MHz | 60 MHz |
|---|---|---|
| Pc2a1pa sym P04218 | r1 = 3.9 r2 = 4.5 | r1 = 3.2 r2 = 3.9 |
| Pc2a1pa asym P04216 | r1 = 3.7 r2 = 4.1 | r1 = 3.2 r2 = 3.7 |
| Pc1a2pa sym P04213 | r1 = 1.9 r2 = 2.1 | r1 = 1.6 r2 = 1.8 |

It is found that the relaxivities observed are of the same order of magnitude as those obtained with the gadolinium-based contrast agents used clinically, for example Dotarem®.

Figure 6:
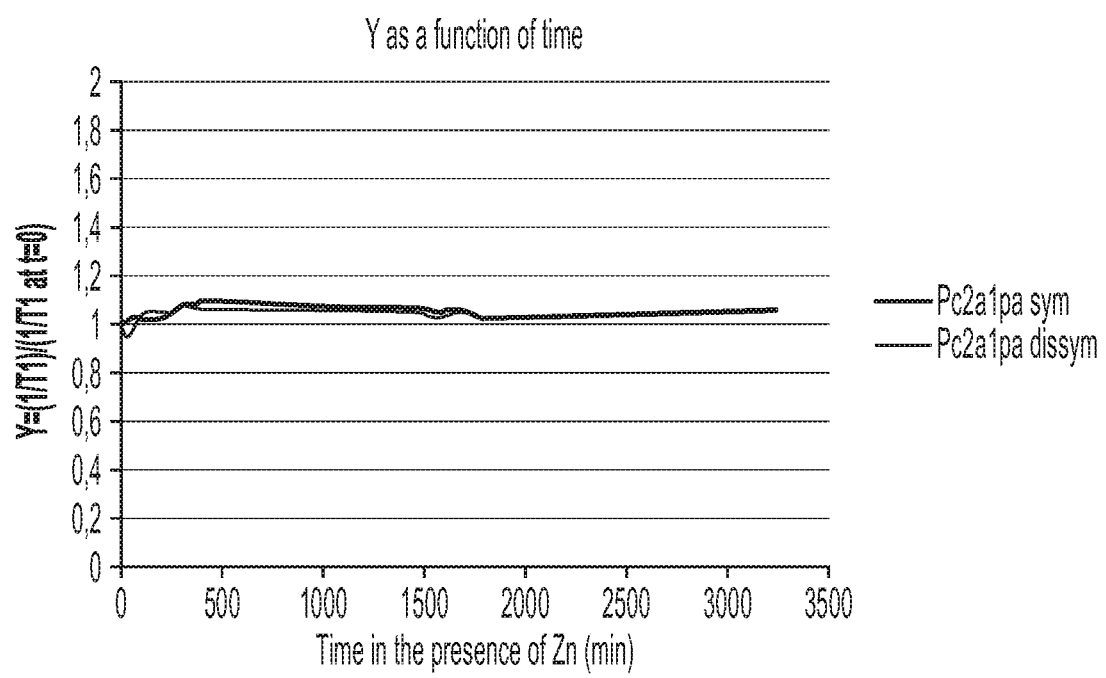
FIG. 6: Ratio between the relaxivity of the gadolinium complexes of ligands P04218 and P04216 measured at a given time and that at t=0 min as a function of time in the presence of a solution of Zn and phosphates.

3) Stability of the Gd Complexes in Competitive Medium:

To a solution comprising the gadolinium complex of ligands P04218 and P04216 at 2.5 mM in phosphate buffer at 333 mM is added a solution of ZnCl$_2$ at 2.5 mM. The relaxivity value of these solutions is measured regularly. The relationship between the relaxivity measured at a given time and that at t=0 min as a function of the time in the presence of the Zn solution is given in FIG. 6. The complexes according to the invention are stable over time.

4) Synthesis and Characterization of the Complexes

General procedure for preparing the lanthanide complexes (Ln=Y$^{3+}$, Gd$^{3+}$, Eu$^{3+}$, Tb$^{3+}$, Yb$^{3+}$, Lu$^{3+}$).

The ligand is dissolved in water and the pH is adjusted to 5 with 1M KOH solution and a solution of the metal chloride (M=Y$^{3+}$, Gd$^{3+}$, Eu$^{3+}$, Tb$^{3+}$, Yb$^{3+}$, Lu$^{3+}$) is then added (1.2 equivalents). The mixture is refluxed overnight and the solution obtained is concentrated.

The complex is purified by preparative chromatography on a column of C-18 grafted silica, eluting with a water/acetonitrile mixture.

| | Abbreviation | Ligand | |
|---|---|---|---|
| Mono S | Pc-2a1pa Sym | P04218 | L1 |
| Mono AS | Pc-2a1pa Asym | P04216 | L3 |
| Di Sym | Pc-1a2pa sym | P04213 | L2 |
| Di AS | Pc-1a2pa Asym | P04214 | L4 |

Synthesis of [ML1(H$_2$O)]

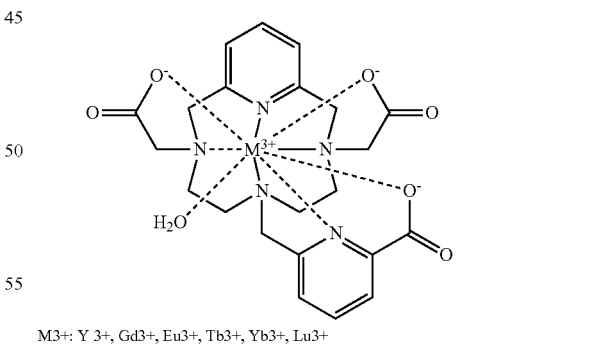

M3+: Y 3+, Gd3+, Eu3+, Tb3+, Yb3+, Lu3+

[YL1(H$_2$O)]

L1.3HCl (27.2 mg, 0.048 mmol), YCl$_3$.6H$_2$O (25.0 mg, 0.082 mmol)

Yield: 24.5 mg, 91%

ESI-HR-MS (positive, H$_2$O) m/z calc. [C$_{22}$H$_{25}$YN$_5$O$_6$]$^+$, 544.0858; measured 544.0858 [M+H]$^+$, calc. [C$_{22}$H$_{26}$YN$_5$O$_6$]$^{2+}$, 272.5465; measured 272.5469 [M+2H]$^{2+}$.

[GdL1(H₂O)]
L1.3HCl (36.5 mg, 0.064 mmol), GdCl₃.6H₂O (27.5 mg, 0.074 mmol)
Yield: 39.8 mg, 98%
ESI-HR-MS (positive, H₂O) m/z calc. $[C_{22}H_{25}GdN_5O_6]^+$, 613.1040; measured 613.1031 $[M+H]^+$, calc. $[C_{22}H_{26}GdN_5O_6]^{2+}$, 307.0557; measured 307.0560 $[M+2H]^{2+}$.

[EuL1(H₂O)]
L1.3HCl (22.0 mg, 0.039 mmol), EuCl₃.6H₂O (17.1 mg, 0.047 mmol)
Yield: 22.1 mg, 91%
ESI-HR-MS (positive, H₂O) m/z calc. $[C_{22}H_{25}EuN_5O_6]^+$, 608.1012; measured 608.1004 $[M+H]^+$, calc. $[C_{22}H_{26}EuN_5O_6]^{2+}$, 304.5542; measured 304.5544 $[M+2H]^{2+}$:

[TbL1(H₂O)]
L1.3HCl (22.0 mg, 0.039 mmol), TbCl₃.6H₂O (17.4 mg, 0.047 mmol)
Yield: 22.6 mg, 95%
ESI-HR-MS (positive, H₂O) m/z calc. $[C_{22}H_{25}TbN_5O_6]^+$, 614.1053; measured 614.1048 $[M+H]^+$, calc. $[C_{22}H_{26}TbN_5O_6]^{2+}$, 307.5563; measured 307.5565 $[M+2H]^{2+}$.

[YbL1(H₂O)]
L1.3HCl (25.0 mg, 0.044 mmol), YbCl₃.6H2O (20.5 mg, 0.053 mmol)
Yield: 27.3 mg, 96%
ESI-HR-MS (positive, H₂O) m/z calc. $[C_{22}H_{25}YbN_5O_6]$, 629.1188; measured 629.1187 $[M+H]^+$, calc. $[C_{22}H_{26}YbN_5O_6]^{2+}$, 315.0630; measured 315.0635 $[M+2H]^{2+}$.

[LuL1(H₂O)]
L1.3HCl (25.0 mg, 0.044 mmol), LuCl₃.6H₂O (20.6 mg, 0.053 mmol)
Yield: 26 mg, 91%
ESI-HR-MS (positive, H₂O) m/z calc. $[C_{22}H_{2}5LuN_5O_6]^+$, 630.1207; found 630.1196 $[M+H]^+$, calc. $[C_{22}H_{26}LuN_5O_6]^{2+}$, 315.5640; found 315.5641 $[M+2H]^{2+}$.

Synthesis of [ML2]

[GdL2]
L2.3HCl (39.0 mg, 0.061 mmol), GdCl₃.6H2O (27.0 mg, 0.073 mmol)
Yield: 41.1 mg, 99%
ESI-HR-MS (positive, H₂O) m/z calc. $[C_{27}H_{28}GdN_6O_6]^+$, 690.1306; measured 690.1313 $[M+H]^+$, calcd. for $[C_{27}H_{29}GdN_6O_6]^{2+}$, 345.5689; measured 345.5690 $[M+2H]^{2+}$.

[EuL2]
L2.3HCl (25.0 mg, 0.039 mmol), EuCl₃.6H₂O (17.1 mg, 0.047 mmol)
Yield: 25.3 mg, 96%
ESI-HR-MS (positive, H₂O) m/z calc. $[C_{27}H_{28}EuN_6O_6]^+$, 685.1277; measured 685.1279 $[M+H]^+$, calc. $[C_{27}H_{29}EuN_6O_6]^{2+}$, 343.0675; measured 343.0680 $[M+2H]^{2+}$.

[TbL2]
L2.3HCl (20.0 mg, 0.031 mmol), TbCl₃.6H₂O (13.9 mg, 0.037 mmol)
Yield: 19.6 mg, 92%
ESI-HR-MS (positive, H₂O) m/z calc. $[C_{27}H_{28}TbN_6O_6]^+$, 691.1318; measured 691.1314 $[M+H]^+$, calc. $[C_{27}H_{29}TbN_6O_6]^{2+}$, 346.0696; measured 346.0697 $[M+2H]^{2+}$.

[YbL2]
L2.3HCl (22.0 mg, 0.034 mmol), YbCl₃.6H₂O (15.9 mg, 0.041 mmol)
Yield: 22.1 mg, 92%
ESI-HR-MS (positive, H₂O) m/z calc. $[C_{27}H_{28}YbN_6O_6]^+$, 706.1453; measured 706.1454 $[M+H]^+$, calc. $[C_{27}H_{29}YbN_6O_6]^{2+}$, 353.5763; measured 353.5764 $[M+2H]^{2+}$.

[LuL2]
L2.3HCl (22.0 mg, 0.034 mmol), LuCl₃.6H₂O (16.0 mg, 0.041 mmol)
Yield: 22.8 mg, 95%
ESI-HR-MS (positive, H₂O) m/z calc. $[C_{27}H_{28}LuN_6O_6]^+$, 707.1473; measured 707.1476 $[M+H]^+$, calc. $[C_{27}H_{29}LuN_6O_6]^{2+}$, 354.0773; measured 354.0776 $[M+2H]^{2+}$.

Synthesis of [ML3(H₂O)]

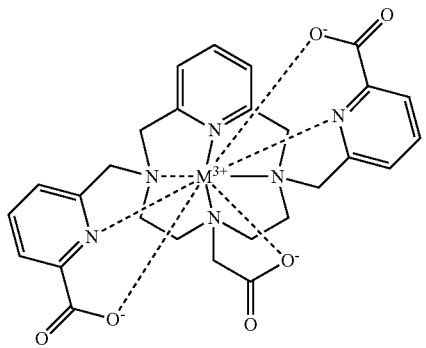

M3+: Y 3+, Gd3+, Eu3+, Tb3+, Yb3+, Lu3+

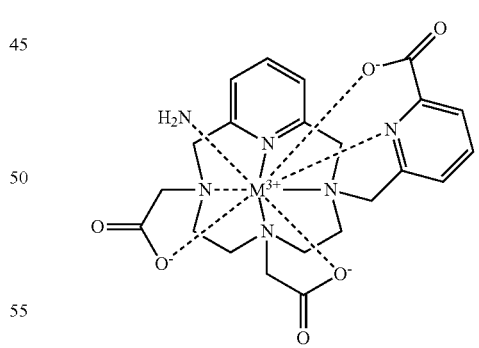

M3+: Y 3+, Gd3+, Eu3+, Tb3+, Yb3+, Lu3+

[YL2]
L2.3HCl (100.0 mg, 0.155 mmol), YCl₃.6H2O (89.0 mg, 0.293 mmol)
Yield: 84.8 mg, 88%
ESI-HR-MS (positive, H₂O) m/z calc. $[C_{27}H_{28}YN_6O_6]^+$, 621.1123; measured 621.1116 $[M+H]^+$, calc. $[C_{27}H_{29}YN_6O_6]^{2+}$, 311.0598; measured 311.0603 $[M+2H]^{2+}$.

[YL3(H₂O)]
L3.3HCl (30.0 mg, 0.053 mmol), YCl₃.6H₂O (24.0 mg, 0.079 mmol)
Yield: 28.0 mg, 94%
ESI-HR-MS (positive, H₂O) m/z calc. $[C_{22}H_{25}YN_5O_6]^+$, 544.0858; measured 544.0859 $[M+H]^+$ calc. $[C_{22}H26YN_5O_6]^{2+}$, 272.5465; measured 272.5469 $[M+2H]^{2+}$.

[GdL3(H₂O)]
L3.3HCl (53.0 mg, 0.093 mmol), GdCl₃.6H2O (41.3 mg, 0.111 mmol)
Yield: 58.7 mg, 99%
ESI-HR-MS (positive, H₂O) m/z calc. $[C_{22}H_{25}GdN_5O_6]^+$, 613.1040; measured 613.1030 $[M+H]^+$, calc. $[C_{22}H_{26}GdN_5O_6]^{2+}$, 307.0557; measured 307.0568 $[M+2H]^{2+}$.

[EuL3(H₂O)]
L3.3HCl (28.5 mg, 0.050 mmol), EuCl₃.6H₂O (22.1 mg, 0.060 mmol)
Yield: 29.0 mg, 92%
ESI-HR-MS (positive, H₂O) m/z calc. $[C_{22}H_{25}EuN_5O_6]^+$, 608.1012; measured 608.1007 $[M+H]^+$, calc. $[C_{22}H_{26}EuN_5O_6]^{2+}$, 304.5542; measured 304.5544 $[M+2H]^{2+}$.

[TbL3(H₂O)]
L3.3HCl (24.0 mg, 0.042 mmol), TbCl₃.6H2O (19.0 mg, 0.051 mmol)
Yield: 23.2 mg, 89%
ESI-HR-MS (positive, H₂O) m/z calc. $[C_{22}H_{25}TbN_5O_6]^+$, 614.1053; measured 614.1049 $[M+H]^+$, calc. $[C_{22}H_{26}TbN_5O_6]^{2+}$, 307.5563; measured 307.5563 $[M+2H]^{2+}$.

[YbL3(H₂O)]
L3.3HCl (25.0 mg, 0.044 mmol), YbCl₃.6H2O (20.5 mg, 0.053 mmol)
Yield: 27.8 mg, 98%
ESI-HR-MS (positive, H₂O) m/z calc. $[C_{22}H_{25}YbN_5O_6]^+$, 629.1188; measured 629.1182 $[M+H]^+$, calc. $[C_{22}H_{26}YbN_5O_6]^{2+}$, 315.0630; measured 315.0634 $[M+2H]^{2+}$.

[LuL3(H₂O)]
L3.3HCl (28.0 mg, 0.049 mmol), LuCl₃.6H₂O (23.1 mg, 0.059 mmol)
Yield: 29 mg, 91%
ESI-HR-MS (positive, H₂O) m/z calc. $[C_{22}H_{25}LuN_5O_6]^+$, 630.1207; measured 630.1204 $[M+H]^+$, calc. [C22H26LuN5O6]²⁺, 315.5640; measured 315.5642 $[M+2H]^{2+}$.

Synthesis of [ML4(H₂O)]

[YL4]
L4.3HCl (30.0 mg, 0.047 mmol), YCl₃.6H₂O (24.0 mg, 0.079 mmol)
Yield: 24.8 mg, 92%
ESI-HR-MS (positive, H₂O) m/z calc. $[C_{27}H_{28}YN_6O_6]^+$, 621.1123; measured 621.1121 $[M+H]^+$, calc. $[C_{27}H_{29}YN_6O_6]^{2+}$, 311.0598; measured 311.0601 $[M+2H]^{2+}$.

[GdL4]
L4.3HCl (36.2 mg, 0.056 mmol), GdCl₃.6H₂O (25.1 mg, 0.068 mmol)
Yield: 38.1 mg, 98%
ESI-HR-MS (positive, H₂O) m/z calc. $[C_{27}H_{28}GdN_6O_6]^+$, 690.1306; measured 690.1321 $[M+H]^+$, calc. $[C_{27}H_{29}GdN_6O_6]^{2+}$, 345.5698; measured 345.5690 $[M+2H]^{2+}$.

[EuL4]
L4.3HCl (23.5 mg, 0.036 mmol), EuCl₃.6H₂O (16.0 mg, 0.044 mmol)
Yield: 21.8 mg, 87%
ESI-HR-MS (positive, H₂O) m/z calc. $[C_{27}H_{28}EuN_6O_6]^+$, 685.1277; measured 685.1277 $[M+H]^+$, calc. $[C_{27}H_{29}EuN_6O_6]^{2+}$, 343.0675; measured 343.0680 $[M+2H]^{2+}$.

[TbL4]
L4.3HCl (24.0 mg, 0.037 mmol), TbCl₃.6H₂O (16.4 mg, 0.044 mmol)
Yield: 25.3 mg, 98%
ESI-HR-MS (positive, H₂O) m/z calc. $[C_{27}H_{28}TbN_6O_6]^+$, 691.1318; measured 691.1316 $[M+H]^+$ calc. $[C_{27}H_{29}TbN_6O_6]^{2+}$, 346.0696; measured 346.0699 $[M+2H]^{2+}$.

[YbL4]
L4.3HCl (30.0 mg, 0.047 mmol), YbCl₃.6H₂O (21.7 mg, 0.056 mmol)
Yield: 30.4 mg, 93%
ESI-HR-MS (positive, H₂O) m/z calc. $[C_{27}H_{28}YbN_6O_6]^+$, 706.1453; measured 706.1454 $[M+H]^+$, calc. $[C_{27}H_{29}YbN_6O_6]^{2+}$, 353.5763; measured 353.5768 $[M+2H]^{2+}$.

[LuL4]
L4.3HCl (30.0 mg, 0.047 mmol), LuCl₃.6H₂O (21.8 mg, 0.056 mmol)
Yield: 30.4 mg, 92%
ESI-HR-MS (positive, H₂O) m/z calc. $[C_{27}H_{28}LuN_6O_6]^+$, 707.1473; measured 707.1470 $[M+H]^+$, calc. $[C_{27}H_{29}LuN_6O_6]^{2+}$, 354.0773; measured 354.0776 $[M+2H]^{2+}$.

C-3 Study in Solution

1) Study by Nuclear Magnetic Resonance:

By way of example, the ¹H NMR spectra of the ligand P04213 and of its yttrium complex P04183 recorded in D₂O are shown in FIG. 1. Relative to the spectrum of the ligand, the presence of the metal cation generates dissymmetry and thus a larger number of signals (cf. FIG. 1).

Figure 2:
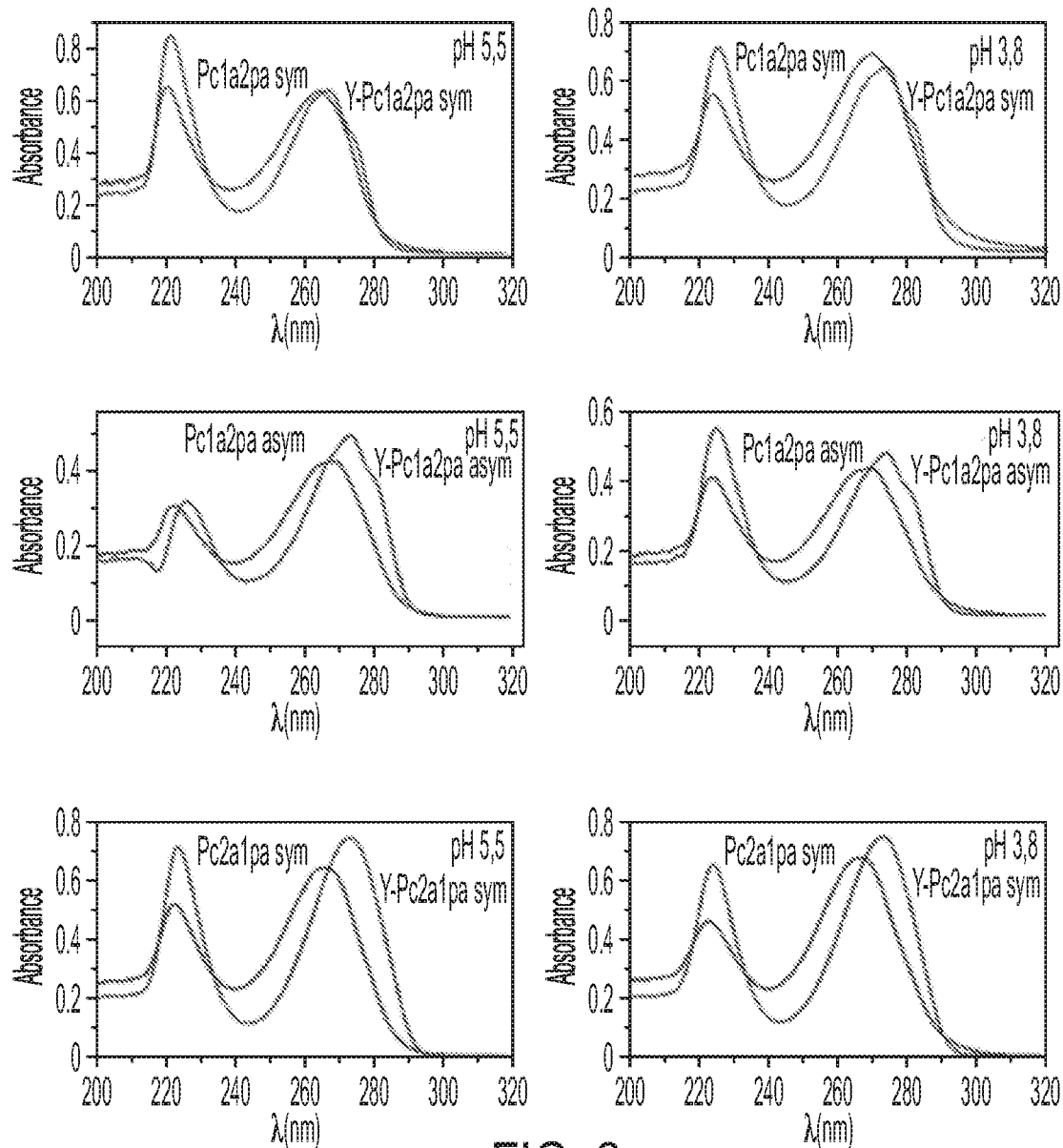
FIG. 2: Absorption spectra of the ligands and of their yttrium complexes recorded in water at pH 3.8 and 5.5 (acetate buffer). The absorption band corresponding to the π-π* transitions of pyridine extends from 240 to 300 nm for the ligands and the complexes.

2) Study by UV-Visible Spectroscopy:

The absorption spectra of the ligands and of their yttrium complexes were recorded in water at pH 3.8 and 5.5 (acetate buffer). The absorption band corresponding to the π-π* transitions of pyridine extend from 240 to 300 nm for the ligands and the complexes (cf. FIG. 2).

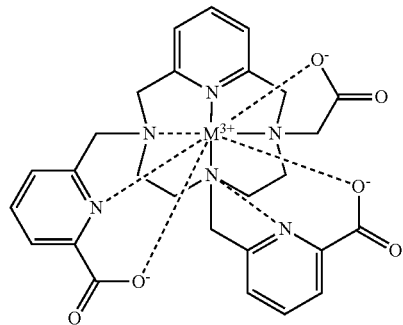

M3+: Y 3+, Gd3+, Eu3+, Tb3+, Yb3+, Lu3+

C-4 Complexation Kinetics

The complexation kinetics of the ligands Pc1a2pa sym P04213, Pc1a2pa asym P04214 and Pc2a1pa sym P04218 with yttrium were studied at pH 3.8 and pH 5.5 in acetate buffer medium by UV-visible spectroscopy. Placed at the absorption maximum of the complex, the increase in absorbance intensity is measured every two seconds until the maximum absorbance is reached. The decrease in intensity of the absorbance at the absorbance maximum of the ligand is monitored when the absorption band of the complex is masked by that of the ligand. For this study, the concentration of the ligands Pc1a2pa sym and Pc1a2pa asym is $4\times10^{-5}$ M and $8\times10^{-5}$ M for the ligand Pc2a1pa sym. At pH 5.5 and 3.8, the ligand Pc1a2pa sym has the fastest complexation kinetics, with total complexation in 30 and 400 seconds, respectively. For the ligands Pc1a2pa asym and Pc2a1pa sym, the complexation is complete in 1100 seconds at pH 3.8 and 100 seconds at pH 5.5.

Figure 3:
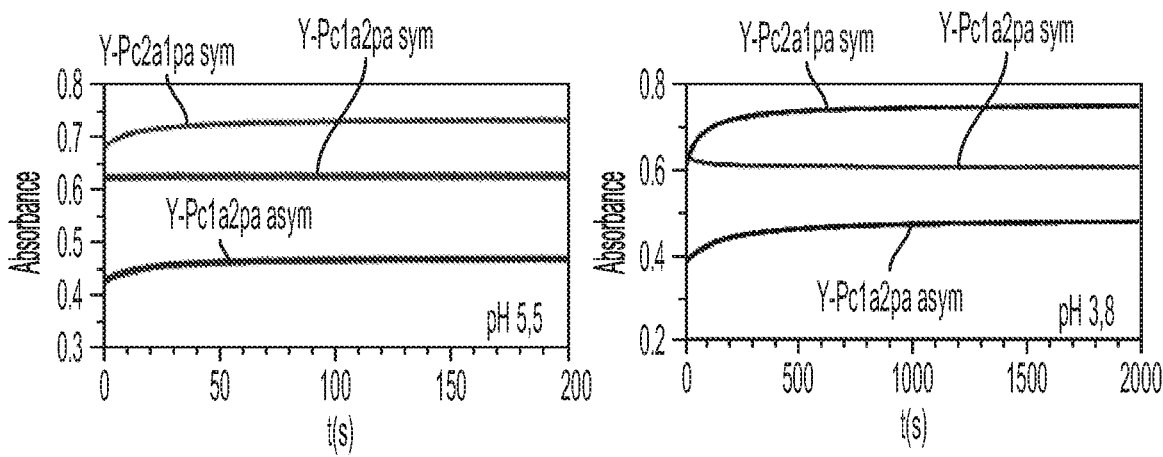
FIG. 3: Monitoring of the variation in absorbance at the Amax of the complex or of the ligand at pH 5.5 and 3.8.
Figure 4:
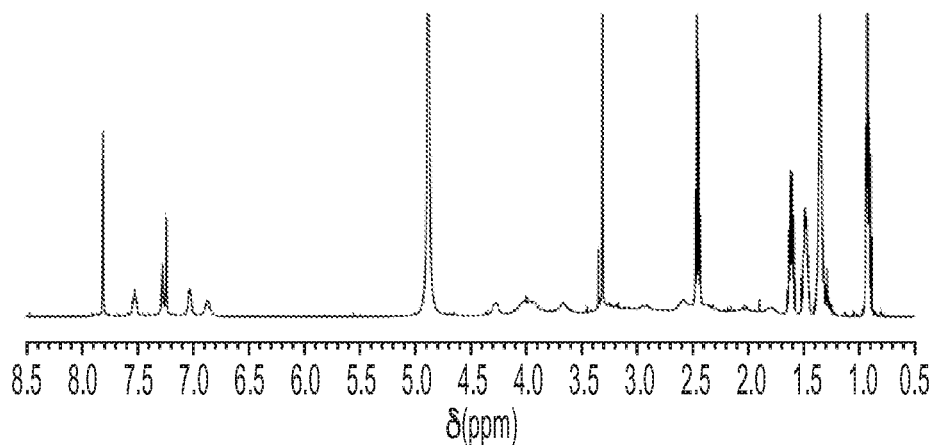
FIG. 4: $^1$H NMR spectrum of the ligand P04330.

Complexation is thus rapid for all of the ligands under the conditions studied. (cf FIG. 3).

C-5 Kinetic Inertia in Competitive Medium

The dissociation kinetics of the complexes in concentrated acidic medium makes it possible to determine the behavior of the complexes in highly competitive medium. The rate of decomplexation is monitored by UV-visible spectroscopy, with $C_{YZ}=4\times10^{-5}$ M for the complexes Y-Pc1a2pa sym P04183, Y-Pc1a2pa asym P04215 and Y-Pc2a1pa sym P04219, in 0.5, 1, 2, 4 and 5M HCl medium. The absorption band of the complex disappears more or less rapidly to reveal the absorption band of the ligand at shorter wavelengths. The plot of the increase in intensity of the absorbance at the absorption maximum of the ligand as a function of time (A=f(t)) makes it possible to determine the half-life times $t_{1/2}$. The $t_{1/2}$ values for the various complexes are listed in the table below. The complexes may be classified in the following manner from the most inert to the least inert: Y-Pc1a2pa asym>>Y-Pc1a2pa sym>Y-PCTA>Y-PCTMB>Y-Pc2a1pa sym. The presence of two picolinate arms on the pyclene macrocycle increases the inertia of the yttrium complex in acidic medium. Furthermore, the inertia of the complex Y-Pc1a2pa asym is greater than that of its symmetrical analog, with, respectively, a $t_{1/2}$ of 433 minutes in 5 M HCl medium, as opposed to 8.5 minutes.

| Ligands $C_{HCl}$ | PCTMB | Pc1a2pa sym | Pc1a2pa asym $t_{1/2}$ (min) | Pc2a1pa sym | PCTA |
|---|---|---|---|---|---|
| 0.5M | 37 | 347 | >1 week (in progress) | 55 | 95 |
| 1M | 20 | 140 | (in progress) | 27 | 39 |
| 2M | 9 | 51 | 2745 | 10.6 | 17 |
| 4M | 3.2 | 13 | 907 | 2.7 | 6.7 |
| 5M | 2.6 | 8.5 | 433 | 0.8 | 3.1 |

C-6 Studies of Thermodynamic Stability by Potentiometry

1) Protonation Constants of the Liqands

Four protonation constants were determined for the ligands Pc1a2pa sym P04213, Pc1a2pa asym P04214, Pc2a1pa sym P04216 and Pc3pa P04221. These values are coherent with those determined for PCTMB (phosphonic acid, P,P',P''-[3,6,9,15-tetraazabicyclo[9.3.1]pentadeca-1(15),11,13-triene-3,6,9-triyltris(methylene)]tris-, P, P', P''-tributyl ester) and also with those described in the literature especially for PCTA (3,6,9,15-tetraazabicyclo[9.3.1]pentadeca-1(15),11,13-triene-3,6,9-triacetic acid), EDTA (ethylenediaminetetraacetic acid) and DOTA (1,4,7,10-tetraazacyclododecane-1,4,7,10-tetraacetic acid).

TABLE 13

| Ligands I | PCTMB 0.1 KNO$_3$ | EDTA [2] 0.1 KNO$_3$ | PCTA [3] 1.0 KCl | DOTA [4] 0.1 Me$_4$NNO$_3$ | Pc1a2pa sym 0.1 KNO$_3$ | Pc1a2pa asym 0.1 KNO$_3$ | Pc2a1pa sym 0.1 KNO$_3$ |
|---|---|---|---|---|---|---|---|
| log $K_t^H$ [HL]/[L][H] | 11.16 | 10.22 | 11.36 | 12.09 | 11.30 | 10.50 | 10.43 |
| [H$_2$L]/[HL][H] | 5.28 | 6.16 | 7.35 | 9.76 | 5.58 | 6.73 | 7.38 |
| [H$_3$L]/[H$_2$L][H] | 1.72 | 2.71 | 3.83 | 4.56 | 4.23 | 3.86 | 3.95 |
| [H$_4$L]/[H$_3$L][H] | — | 2.0 | 2.12 | 4.09 | 3.01 | 2.98 | 2.15 |
| [H$_5$L]/[H$_4$L][H] | — | — | 1.29 | — | — | — | — |
| Σlog $K_i$ | 18.15 | 21.09 | 25.95 | 30.50 | 24.12 | 24.06 | 23.90 |

For the derivative Pc3pa P04221, the values obtained are as follows:

TABLE 14

| | Pc3pa P04221 | |
|---|---|---|
| $\log K^H_i$ | [HL]/[L][H] | 10.03 |
| | [H$_2$L]/[HL][H] | 5.95 |
| | [H$_3$L]/[H$_2$L][H] | 3.82 |
| | [H$_4$L]/[H$_3$L][H] | 2.98 |

2) Stability Constants of the Complexes

The thermodynamic protonation and stability constants of the complexes were determined by potentiometry at 25° C. with control of the ionic strength (I=0.1 M KNO$_3$). Refinement of the titration curves with the HyperQuad software makes it possible to determine the overall constants (log β), from which the partial constants (log K) are calculated.

The stability constants of the ligands Pc1a2pa sym P04213, Pc1a2pa asym P04214 et Pc2a1pa sym P04218 and P04221 with yttrium were determined by direct potentiometric titration. The log $K_{YL}$ constant values for the ligands Pc1a2pa sym, Pc1a2pa asym and Pc2a1pa sym are, respectively, 19.78, 19.49 and 19.28, and the log $K_{YLH}^{-1}$ constant values are 11.84, 11.79 and 10.60.

For Pc3pa P04222, the pM calculated is 14.7.

The speciation diagrams, plotted from the thermodynamic stability constants of the yttrium complexes, indicate that the complexes exist exclusively in the form YL over a wide pH range, including at pH 7.4.

REFERENCES

1 Aime, S.; Botta, M.; Geninatti Crich, S.; Giovenzana, G. B.; Jommi, G.; Pagliarin, R.; Sisti, M. *Inorg. Chem.* 1997, 36, 2992-3000.

2 Delgado, R.; Figueira, C.; Quintino, S. *Talanta* 1997, 45, 451.

3 Tircsó, G.; Kovacs, Z.; Dean Sherry, A. *Inorg. Chem.* 2006, 45, 9269.

4 Chaves, S.; Delgado, R.; Frausto da Silva, J. J. R. *Talanta* 1992, 39, 249.

5 Kumar, K.; Chang C. A.; Francesconi, L. C.; Dischino, D. D.; Malley, M. F.; Gougoutas, J. Z.; Tweedle, M. F. *Inorg. Chem.* 1994, 33, 3567.

| | Reaction equilibrium | PCTMB [b] | EDTA [c] | PCTA [f] | DOTA [g] | Pc1a2pa sym | Pc1a2pa asym | Pc2a1pa sym |
|---|---|---|---|---|---|---|---|---|
| Log $K_{MHiL}$ Y$^{3+}$ | [ML]/[M][L] | 19.49 | 18.5 [d] | 20.28 | 24.9 [h] | 19.78 | 19.49 | 19.28 |
| | [MHL]/[ML][H] | 3.45 | — | 1.81 | — | — | — | — |
| | [ML]/[MLOH][H] | 9.10 | — | 11.10 | — | 11.84 | 11.79 | 10.60 |

[a] For the sake of claritiy, the charges are not indicated.
[b] Values determined by competition with EDTA. 0.1M KNO$_3$.
[c] Ref 2, 0.1M KNO$_3$.
[d] Ref 5, 0.1M NMe$_4$Cl.
[e] Ref 6, 0.1M KNO$_3$.
[f] Ref 3, 1.0M KCl.
[g] Ref 4, 0.1M NMe$_4$Cl.
[h] Ref 7, 0.1M NMe$_4$NO$_3$.

TABLE 16

| | Pc3pa + Y$^{3+}$P04222 | |
|---|---|---|
| log$K_{MHiL}$ | ML]/[M][L] | 16.42 |
| | [MHL]/[ML][H] | 3.11 |
| | [ML]/[MLOH][H] | 11.02 |

These stability constants are not comparable as such: the basicity of the ligands needs to be taken into account. The constant pM=−log[M] is used for this purpose. It is calculated from the protonation constants of the ligands and the stability constants of the complexes with CL=10×CM=10$^{-5}$ M at pH 7.4. The ligand Pc1a2pa asym P04214 has a p(Y) of 17.3, which is higher than that of PCTA (p(Y)=17.0), of Pc1a2pa sym P04213 (p(Y)=16.8) and of Pc2a1pa sym P04218 (p(Y)=16.9). The highest p(Y) nevertheless remains that of DOTA, with a value of 18.8.

6 Delgado, R.; Frausto da Silva, J. J. R. *Talanta* 1982, 29, 815.

7 Cox, J. P. L.; Jankowski, K. J.; Kataky, R.; Parker, D.; Beeley, N. R. A.; Boyce, B. A.; Eaton, M. A. W.; Millar, K.; Millican, A. T.; Harrison, A.; Walkerc, C. *J. Chem. Soc. Chem. Commun.* 1989, 797.

C-7 Solid-State Study

The yttrium complex P04183 crystallizes in water. The structure obtained by x-ray diffraction is presented below. The metal is coordinated to the four nitrogen atoms of the macrocycle, the two nitrogen atoms of the picolinate arms and the three oxygen atoms of the carboxylic acids. The coordination sphere of the metal is N6O3, i.e. 9 coordinant atoms. The helicities Δ and Λ derived from the orientation of the picolinate and acetate arms are both present: the complex thus crystallizes as a racemic mixture.

TABLE 17

| | | | pM = −log[M] [a] | | | | |
|---|---|---|---|---|---|---|---|
| Ligands | PCTMB | EDTA | PCTA | DOTA | Pc1a2pa sym | Pc1a2pa asym | Pc2a1pa sym |
| pY | 16.7 | 16.6 | 17.0 | 18.8 | 16.8 | 17.3 | 16.9 |

[a] Values calculated from the constants of the preceding tables. with $C_L$ = 10 × $C_M$ = 10$^{-5}$ M à pH 7.4.

The invention claimed is:
1. A compound of general formula (X)

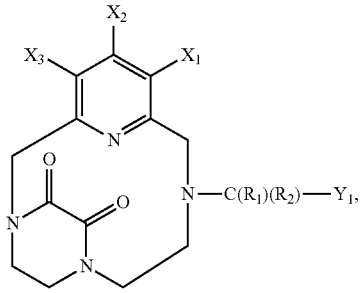

in which:
R₁ and R₂ represent, independently of each other, one of the following:
H, a (C₁-C₂₀)alkyl group or a (C₁-C₂₀)alkylene-(C₆-C₁₀)aryl group, wherein said alkyl, alkylene and aryl groups optionally are substituted with one or more organic acid functions;
X₁, X₂ and X₃ represent, independently of each other, one of the following:
H, —C(O)N(Re)(Rd), a (C₁-C₂₀)alkyl, a (C₂-C₂₀)alkenyl, a (C₂-C₂₀)alkynyl and a (C₆-C₁₀)aryl, with Re and Rd being, independently of each other, H or a (C₁-C₂₀) alkyl group, wherein said alkyl, alkenyl and alkynyl groups optionally comprise one or more heteroatoms and/or one or more (C₆-C₁₀)arylenes in their chains, and wherein said alkyl, alkenyl and alkynyl groups optionally are substituted with a (C₆-C₁₀)aryl;
wherein said alkyl, alkenyl, alkynyl and aryl groups optionally are substituted with one or more organic acid functions; and
Y₁ represents a C(O)OH group, a protected form of the C(O)OH group in which the hydrogen is replaced with an alkyl, or a group of formula (II)

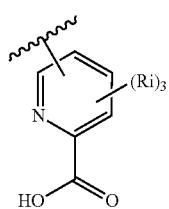

in which the radicals Ri represent, independently of each other, one of the following:
H, halogen, N₃, (C₁-C₂₀)alkyl, (C₂-C₂₀)alkenyl, (C₂-C₂₀)alkynyl and (C₆-C₁₀)aryl, wherein said alkyl, alkenyl and alkynyl groups optionally comprise one or more heteroatoms and/or one or more (C₆-C₁₀) arylenes in their chains and, wherein said alkyl, akenyl, and alkynyl groups optionally are substituted with a (C₆-C₁₀) aryl;
wherein said alkyl, alkenyl, alkynyl and aryl groups optionally are substituted with one or more organic acid functions.
2. The compound of claim 1, wherein X₁, X₂ and X₃ represent, independently of each other, one of the following:
H, (C₁-C₂₀)alkyl, (C₂-C₂₀)alkenyl and (C₂-C₂₀)alkynyl, wherein said alkyl, alkenyl and alkynyl groups optionally comprise one or more heteroatoms in their chain.
3. The compound of claim 2, wherein X₁, X₂ and X₃ are H.
4. The compound of claim 1, wherein the organic acid functions optionally substituting the alkyl, alkenyl, alkynyl and aryl groups of the X₁, X₂ and X₃ are, independently of each other, one of the following:
—COOH, —SO₂OH, —P(O)(OH)₂ and —O—P(O)(OH)₂.
5. The compound of claim 1, wherein R₁ and R₂ represent, independently of each other, H or (C₁-C₂₀)alkyl group.
6. The compound of claim 5, wherein R₁ and R₂ represent H.
7. The compound of claim 1, wherein the organic acid functions optionally substituting the alkyl, alkylene and aryl groups of R₁ and R₂ represent, independently of each other, one of the following:
—COOH, —SO₂OH, —P(O)(OH)₂ and —O—P(O)(OH)₂.
8. The compound of claim 1, wherein the radicals Ri represent, independently of each other, one of the following:
H, (C₁-C₂₀)alkyl, (C₂-C₂₀)alkenyl and (C₂-C₂₀)alkynyl, wherein said alkyl, alkenyl and alkynyl groups optionally comprise one or more N, O and S heteroatoms.
9. The compound of claim 1, wherein the radicals Ri represent, independently of each other, H or (C₂-C₁₅)alkynyl.
10. The compound of claim 1, wherein the organic acid functions substituting the alkyl, alkenyl, alkynyl and aryl groups of the radicals Ri represent, independently of each other, one of the following:
—COOH, —SO₂OH, —P(O)(OH)₂ and —O—P(O)(OH)₂.
11. The compound of claim 10, wherein the organic acid functions substituting the alkyl, alkenyl, alkynyl and aryl groups of the radicals Ri represent —COOH.
12. The compound of claim 1, wherein the group of formula (II) is the following group:

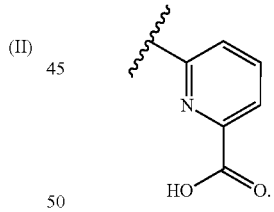

13. The compound of claim 1, wherein:
R₁ and R₂ represent H; and
Y₁ represents C(O)OH or the following formula:

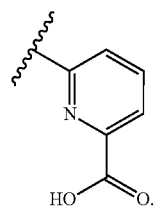 [SMILES: *c1cccc(C(=O)O)n1]

14. A method of preparing the compound of claim 1, the method comprising:

functionalizing a compound of general formula (IX)

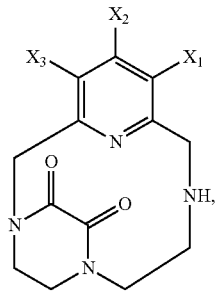

(IX)

by adding to the nitrogen atom of the NH group thereof a —C($R_1$)($R_2$)—$Y_1$ group wherein:
- $R_1$ and $R_2$ represent, independently of each other, one of the following: H, a ($C_1$-$C_{20}$)alkyl group or a ($C_1$-$C_{20}$)alkylene-($C_6$-$C_{10}$)aryl group, wherein said alkyl, alkylene and aryl groups optionally are substituted with one or more organic acid functions;
- $Y_1$ represents a C(O)OH group, a protected form of the C(O)OH group in which the hydrogen is replaced with an alkyl, or a group of formula (II)

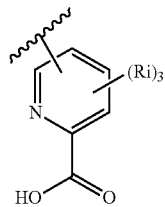

(II)

in which the radicals Ri represent, independently of each other, one of the following:
H, halogen, $N_3$, ($C_1$-$C_{20}$)alkyl, ($C_2$-$C_{20}$)alkenyl, ($C_2$-$C_{20}$)alkynyl and ($C_6$-$C_{10}$)aryl, wherein said alkyl, alkenyl and alkynyl groups optionally comprise one or more heteroatoms and/or one or more ($C_6$-$C_{10}$) arylenes in their chains and, wherein said alkyl, akenyl, and alkynyl groups optionally are substituted with a ($C_6$-$C_{10}$)aryl;
wherein said alkyl, alkenyl, alkynyl and aryl groups optionally are substituted with one or more organic acid functions; to form the compound (X) of claim 1.

15. The compound of claim 1, wherein the alkyl that replaced the hydrogen of the protected form of the C(O)OH group of $Y_1$ is selected from the group consisting of tert-butyl and methyl.

* * * * *